US010711268B2

(12) United States Patent
Murakami et al.

(10) Patent No.: US 10,711,268 B2
(45) Date of Patent: Jul. 14, 2020

(54) METHOD FOR PRODUCING PEPTIDE LIBRARY, PEPTIDE LIBRARY, AND SCREENING METHOD

(71) Applicants: The University of Tokyo, Tokyo (JP); PeptiDream Inc., Kanagawa (JP)

(72) Inventors: Hiroshi Murakami, Tokyo (JP); Takashi Kawakami, Tokyo (JP); Patrick Reid, Tokyo (JP); Toru Sasaki, Tokyo (JP)

(73) Assignees: The University of Tokyo, Tokyo (JP); PeptiDream Inc., Kanagawa (JP)

( * ) Notice: Subject to any disclaimer, the term of this patent is extended or adjusted under 35 U.S.C. 154(b) by 1154 days.

(21) Appl. No.: 14/889,868

(22) PCT Filed: May 12, 2014

(86) PCT No.: PCT/JP2014/062604
§ 371 (c)(1),
(2) Date: Mar. 7, 2016

(87) PCT Pub. No.: WO2014/181888
PCT Pub. Date: Nov. 13, 2014

(65) Prior Publication Data
US 2016/0272964 A1 Sep. 22, 2016

(30) Foreign Application Priority Data
May 10, 2013 (JP) .................................. 2013-100661

(51) Int. Cl.
*C12N 15/10* (2006.01)
*C12N 15/67* (2006.01)
(52) U.S. Cl.
CPC ......... *C12N 15/1062* (2013.01); *C12N 15/67* (2013.01)
(58) Field of Classification Search
None
See application file for complete search history.

(56) References Cited

U.S. PATENT DOCUMENTS

| 5,270,170 A * | 12/1993 | Schatz .................. G01N 33/68 435/252.33 |
|---|---|---|
| 2013/0178394 A1 | 7/2013 | Suga et al. |
| 2013/0021759 A1 | 8/2013 | Suga et al. |

FOREIGN PATENT DOCUMENTS

| WO | 2012026566 A1 | 3/2012 |
|---|---|---|
| WO | 2012033154 A1 | 3/2012 |

OTHER PUBLICATIONS

Dooley et al (Science 23:2019-22). (Year: 1994).*
Fields et al (Biopolymers—Peptide Science 40:345-57) (Year: 1996).*
Goto, et al., "Flexizymes for genetic code reprogramming", Jun. 1, 2011, pp. 779-790, vol. 6, No. 6, Publisher: Nature Protocols, Nature Publishing Group.
Ito, et al., "Technologies for the synthesis of mRNA coding libraries and discovery of bioactive natural product-inspired non-traditional macrocyclic peptides", Mar. 18, 2013, pp. 3502-3528, vol. 18, No. 3, Publisher: Molecules.
Morimoto, et al., "Flexizymes: their evolutionary history and origin of catalytic function", Dec. 20, 2011, pp. 1359-1368, vol. 44, No. 12, Publisher: Accounts of Chemical Research.
Ouchi, et al., "The flexizyme system: a highly flexible tRNA aminoacylation tool for the translation apparatus", Oct. 1, 2007, vol. 11, No. 5, Publisher: Current Opinion in Chemical Biology.
Fujino, et al., "Reevaluation of the D-Amino Acid Compatibility with the Elongation Event in Translation", Jan. 9, 2013, pp. 1830-1837, vol. 135, Publisher: J. Am. Chem. Soc.
Kang, et al, "Translation of a histone H3 tail as a model system for studying peptidyl-tRNA drop-off", May 27, 2011, pp. 2269-2274, vol. 585, Publisher: FEBS Lett.
Josephson, et al., "Ribosomal Synthesis of Unnatural Peptides", Jul. 28, 2005, pp. 1172711735, vol. 127, No. 33, Publisher: J. Am. Chem. Soc.
Kawakami , et al., "Genetically Encoded Libraries of Nonstandard Peptides", Aug. 12, 2012, pp. 1-15, vol. 2012, No. Article ID 713510, Publisher: Journal of Nucleic Acids.

(Continued)

*Primary Examiner* — Christopher M Gross
(74) *Attorney, Agent, or Firm* — Suzannah K. Sundby, Esq.; Canady + Lortz LLP

(57) ABSTRACT

An object of the present invention is to provide a method for producing a peptide library capable of incorporating an arbitrary number of arbitrary proteinogenic and/or non-proteinogenic amino acids in an arbitrary site. The invention provides a method for producing a peptide library including $1 \times 10^6$ or more kinds of peptides containing amino acids encoded by $N_1N_2N_3$, including a step of preparing an mRNA library including mRNAs which encode peptides of the peptide library and each contain at least one $N_1N_2N_3$; and a step of translating each mRNA of the mRNA library in a cell-free translation system added with tRNA containing an anticodon to any one of $N_1N_2N_3$ codons and charged with an amino acid corresponding to the codon (wherein, $N_1$, $N_2$, and $N_3$ are each independently selected from adenine (A), guanine (G), cytosine (C), and uracil (U) and an arbitrary amino acid is reassigned to each $N_1N_2N_3$).

18 Claims, 10 Drawing Sheets

Specification includes a Sequence Listing.

(56) References Cited

OTHER PUBLICATIONS

Ohta, et al., "Synthesis of Polyester by Means of Genetic Code Reprogramming", Dec. 26, 2007, pp. 1315-1322, vol. 14, No. 12, Publisher: Chemistry & Biology.

Anthony C. Forster, "Synthetic biology challenges long-held hypotheses in translation, codon bias and transcription", May 8, 2012, pp. 835-845, vol. 7, Publisher: Biotechnol. J.

Hartman, et al., "An Expanded Set of Amino Acid Analogs for the Ribosomal Translation of Unnatural Peptides", Oct. 3, 2007, p. e972, vol. 2, No. 10, Publisher: PLoS One.

Hartman, et al., "Enzymatic aminoacylation of tRNA with unnatural amino acids", Mar. 21, 2006, pp. 43564361, vol. 103, No. 12, Publisher: PNAS USA.

Ishizawa, et al., "TRAP display: a high-speed selection method for the generation of functional polypeptides", Mar. 18, 2013, pp. 5433-5440, vol. 135, No. 14, Publisher J. Am. Chem. Soc.

Kawakami, et al., "Iden Ango o Reprogramming shite Tokushu Peptide o Tsukuru" (2007) pp. 68-69, vol. 62, No. 8, Publisher: Chemistry.

Kawakami, et al., "Messenger RNA-programmed incorporation of multiple N- methyl-amino acids into linear and cyclic peptides" (2008) pp. 32-42, vol. 15, No. 1, Publisher: Che. Biol.

Kawakami, et al., "Extensive reprogramming of the generic code for genetically encoded synthesis of highly N-alkylated polycyclic peptidomimetics", Jul. 30, 2013, pp. 12297-12304, vol. 135, No. 33, Publisher: J. Am. Chem. Soc.

Murakami, et al., "A highly flexible tRNA acylation method for non-natural polypeptide synthesis,", Apr. 20, 2006, pp. 357-359, vol. 3, No. 5, Publisher: Nat. Mathods.

Murakami, et al., "Expansion and reprogramming of genetic code by Flexizyme" (2006) pp. 2496-2501, vol. 51, No. 16, Publisher: Protein, nucleic acid and enzyme.

Murakami, et al., "RAPID System: Tokushu Peptide Library no Sosei" (2008) pp. 4848-4849, 2U12, vol. 57, No. 2, Publisher: Dai 57 Kai Symposium on Macromolecules Yokoshu (English Abstract).

Murakami, et al., "Flexizyme o Mochiita Tokushu Peptide no Hon'yaku Gosei" (2008) p. 1633 5 SB-07, Publisher: 88th Annual Meeting of the Chemical Society of Japan in Spring Koen Yokoshu II (partial English translation).

Yamagishi, et al., "Natural product-like macrocyclic N-methyl-peptide inhibitors against a ubiquitin ligase uncovered from a ribosome-expressed de novo library", Dec. 13, 2011, pp. 1562-1570, vol. 18, No. 12, Publisher: Chem. Biol.

Zhang, et al., "Specificity of Translation for N-Alkyl Amino Acids", Aug. 25, 2007, pp. 11316-11317, vol. 129 Publisher: J. Am. Chem. Soc.

International Search Report received in PCT/JP2014/062604, dated Aug. 5, 2014.

* cited by examiner

FIG. 1A
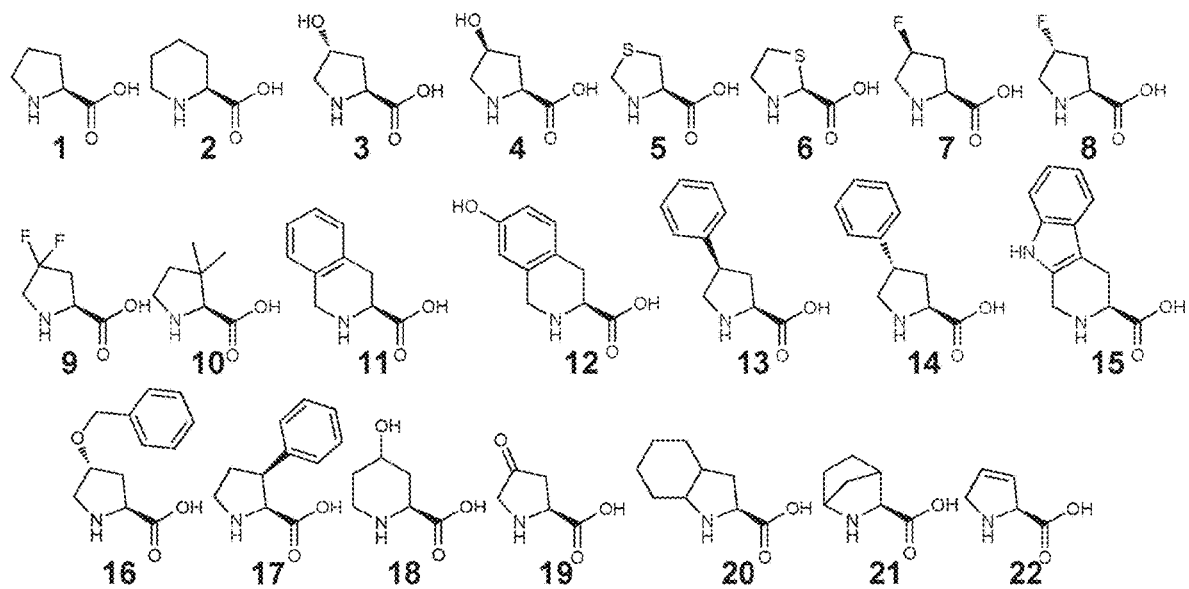
FIG. 1B
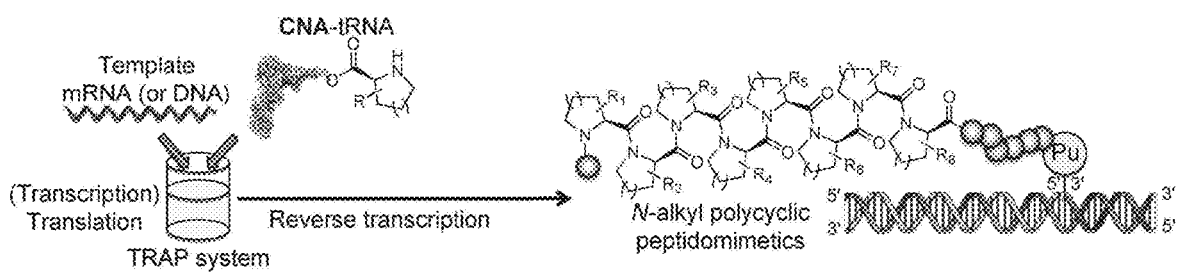
FIG. 1C
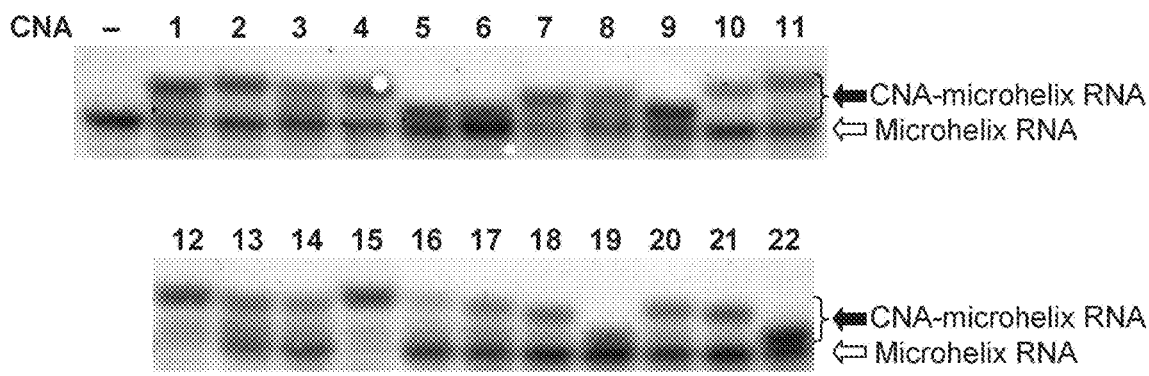
FIG. 2A
mRNA1    5'UTR AUG (AAG)₃ UCC (Flag) UAA 3'UTR
Peptide1    fMet | Lys |₃ CNA | Flag | Stop

FIG. 3D
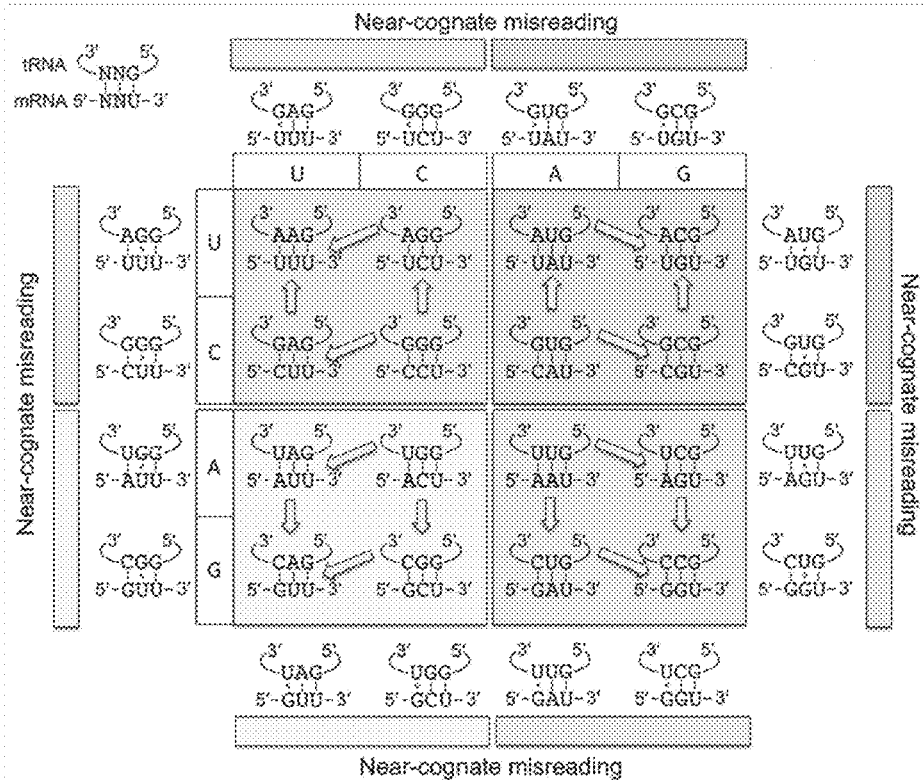
FIG. 4A
| | | | | | | | | |
|---|---|---|---|---|---|---|---|---|
| mRNA10 | 5'UTR AUG (UAG)₃ CUU UUU CCU AGG (UAG)₃ UAA 3'UTR |
| Peptide10 | fMet | Tyr₃ | 8 | 12 | 3 | Arg | Tyr₃ | Stop |
| mRNA11 | 5'UTR AUG (UAG)₃ UUU UCU CCU AGG (UAG)₃ UAA 3'UTR |
| Peptide11 | fMet | Tyr₃ | 12 | 1 | 3 | Arg | Tyr₃ | Stop |
| mRNA12 | 5'UTR AUG (UAG)₃ CUU UCU CCU AGG (UAG)₃ UAA 3'UTR |
| Peptide12 | fMet | Tyr₃ | 8 | 1 | 3 | Arg | Tyr₃ | Stop |
| mRNA13 | 5'UTR AUG (UAG)₃ CUU UUU UCU AGG (UAG)₃ UAA 3'UTR |
| Peptide13 | fMet | Tyr₃ | 8 | 12 | 1 | Arg | Tyr₃ | Stop |
FIG. 4B
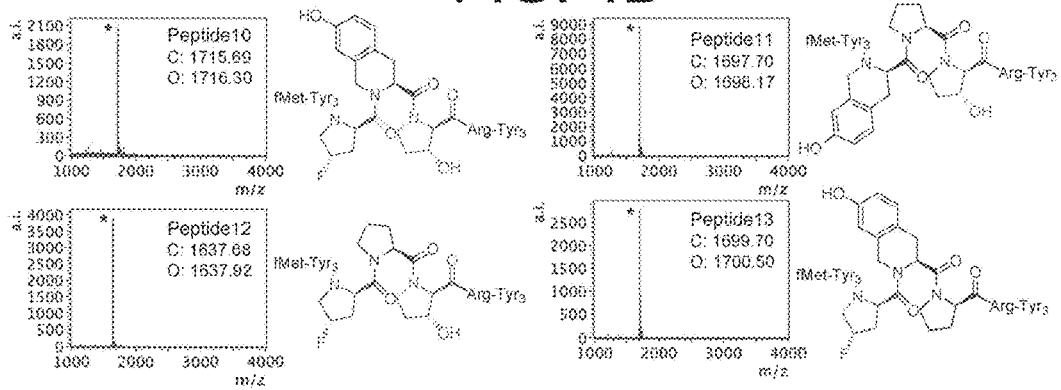

FIG. 5A mRNA14  5'UTR AUG (UAG)₃ CUU UUU UCU CCU AGG (UAG)₃ UAA 3'UTR
Peptide14  |fMet| |Tyr|₃ |8| |12| |1| |3| |Arg| |Tyr|₃ |Stop| mRNA15  5'UTR AUG (UAG)₃ UAU UGU CGU CAU AGG (UAG)₃ UAA 3'UTR
Peptide15  |fMet| |Tyr|₃ |10| |9| |6| |14| |Arg| |Tyr|₃ |Stop| mRNA16  5'UTR AUG (UAG)₃ GUU ACU AUU GCU AGG (UAG)₃ UAA 3'UTR
Peptide16  |fMet| |Tyr|₃ |7| |22| |2| |13| |Arg| |Tyr|₃ |Stop| mRNA17  5'UTR AUG (UAG)₃ AAU AGU GGU GAU AGG (UAG)₃ UAA 3'UTR
Peptide17  |fMet| |Tyr|₃ |19| |16| |4| |5| |Arg| |Tyr|₃ |Stop|

FIG. 5B

| 1st | 2nd U | 2nd C | 2nd A | 2nd G | 3rd |
|---|---|---|---|---|---|
| U | 12 | 1 | 10 | 9 | U/C/A/G |
|   |    |   | Stop/Tyr |   |   |
| C | 8 | 3 | 14 | 6 | U/C/A/G |
| A | 2 | 22 | 19 | 16 | U/C/A/G |
|   | fMet |   |   | Arg |   |
| G | 7 | 13 | 5 | 4 | U/C/A/G |

FIG. 5C

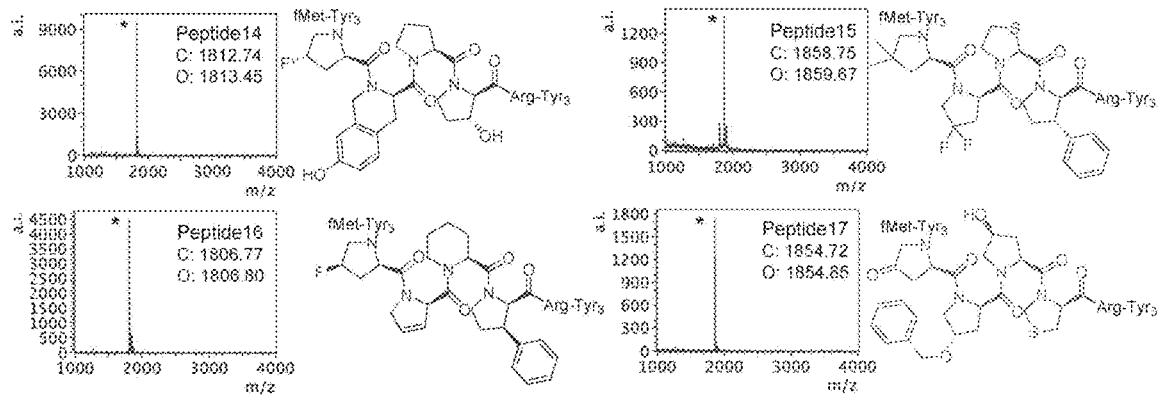

FIG. 6A

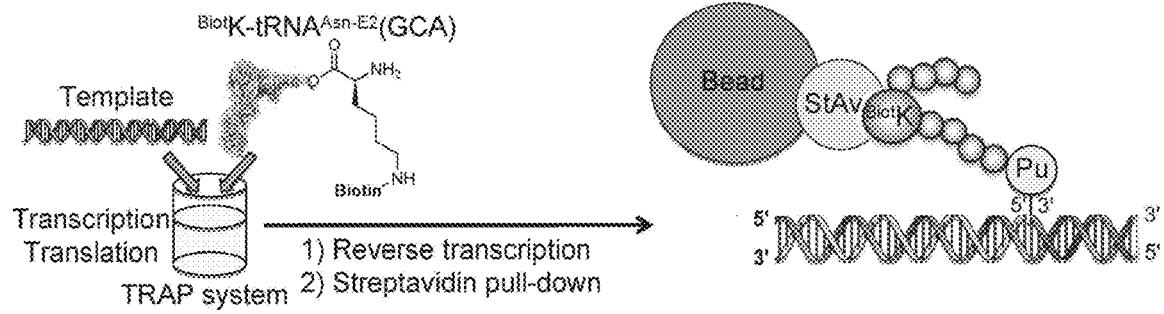

FIG. 6B mRNA libraries  5'UTR AUG (NNU)₃ UGC (XXG)₄ UAG GACGGGGGGCGGGAGGCGGG -3'
Peptide libraries  fMet Xaa₃ BiotK aa₄

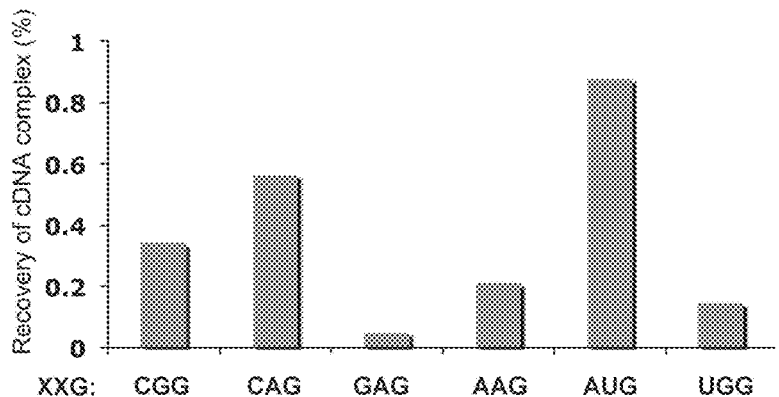

FIG. 6C mRNA library 1  5'UTR AUG (NNU)₃ UGG AUG AUG AUG AUG UAG GACGGGGGGCGGGAGGCGGG -3'
Peptide library 1  fMet Xaa₃ BiotK Met Met Met Met mRNA library 2  5'UTR AUG (NNU)₃ UGG AUG AUG AUG UAG UAG GACGGGGGGCGGGAGGCGGG -3'
Peptide library 2  fMet Xaa₃ BiotK Met Met Met mRNA library 3  5'UTR AUG (NNU)₃ UGG AUG AUG UAG UAG UAG GACGGGGGGCGGGAGGCGGG -3'
Peptide library 3  fMet Xaa₃ BiotK Met Met mRNA library 4  5'UTR AUG (NNU)₃ UGG AUG UAG UAG UAG UAG GACGGGGGGCGGGAGGCGGG -3'
Peptide library 4  fMet Xaa₃ BiotK Met mRNA library 5  5'UTR AUG (NNU)₃ UGG UAG UAG UAG UAG UAG GACGGGGGGCGGGAGGCGGG -3'
Peptide library 5  fMet Xaa₃ BiotK

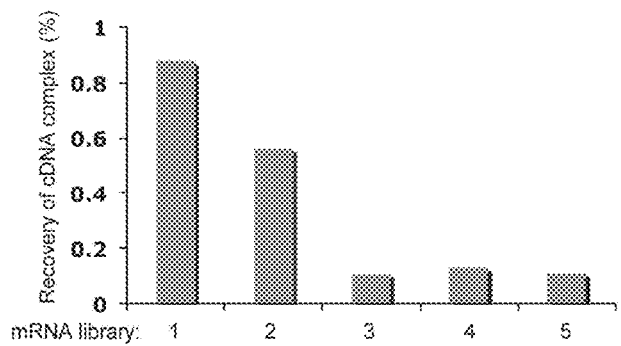

FIG. 7A

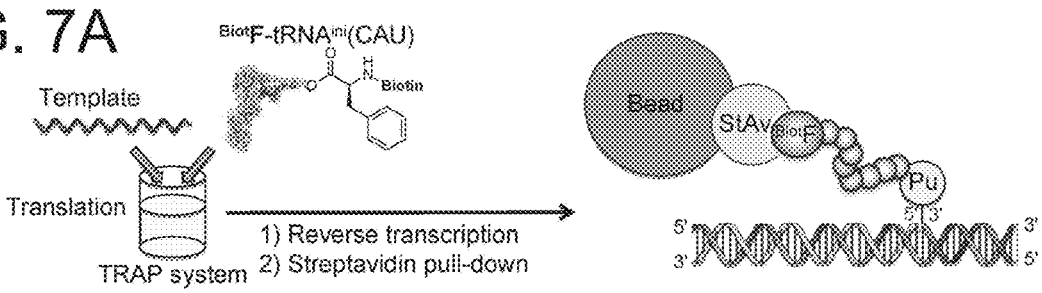

mRNA library 5'UTR AUG (NNU)₈ UGG (AUG)₄ <u>UAG</u> GACGGGGGGCGGGAGGCGGG -3'
Peptide library [BiotF] [Xaa]₈ [Trp] [Ser]₄

Codon table for proteinogenic peptides     Codon table for N-alkyl polycyclic peptidomimetics Initiator

| Peptides | Codon table | Display efficiency |
|---|---|---|
| Proteinogenic peptides | 1 | 10.7% |
| N-alkyl polycyclic peptidomimetics | 2 | 1.9% |

FIG. 8

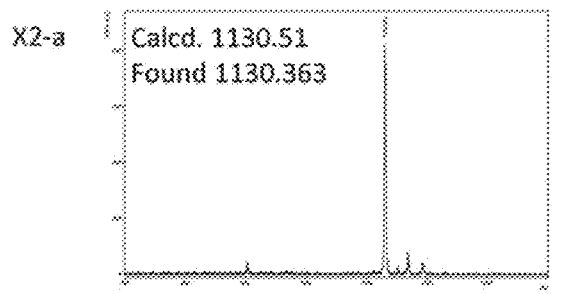

cyclo (Ac-Phe-Ala-Lys-^MePhe-His-Tyr-^PheEtGly-Cys)-OH
AUG   AUU   AAU   GAU   ACC   GCU   AGC   AUG

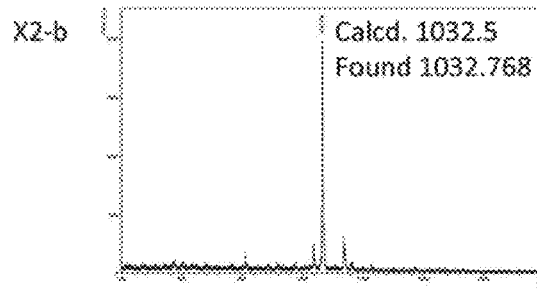

cyclo (Ac-Phe-Arg-Ala-His(3-Me)-^MePhe-Gly-^MeNle-Cys)-OH
AUG   CUU   AUU   UUU   GAC   UCU   CAC   AUG

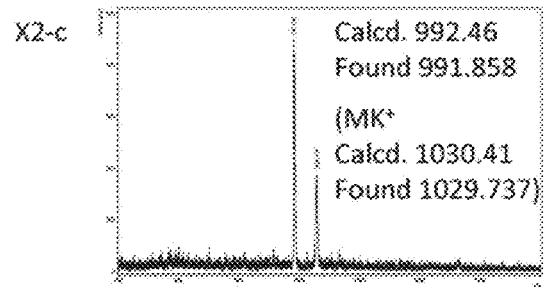

cyclo (Ac-Phe-Gly-Lys-^MeAla-His-Tyr-^BuGly-Cys)-OH
AUG   UCU   AAU   GUU   ACC   GCU   CGU   AUG

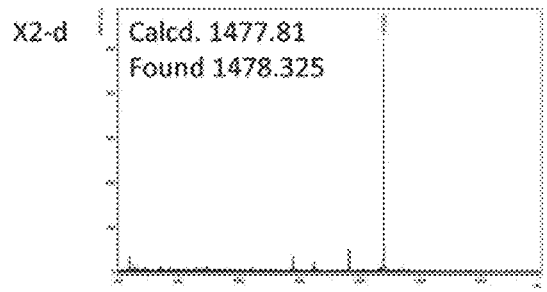

Ac-Ala-Tyr-Ala-Lys-Ala-His-Ile-Arg-Ala-His-Ala-Arg-Ala-OH
AUG  GCU  AUU  AAU  AUU  ACU  UAU  CUU  AUC  ACC  AUU  CUC  AUC

Ac-: N-TERMINAL ACETYL GROUP
-OH: OH OF C-TERMINAL CARBOXYL GROUP
cyclo (Ac-X---Cys): THIOETHER STRUCTURE FORMED FROM CHLOROACETYL AND THIOL GROUP OF Cys

SEQUENCE LISTING

<160> NUMBER OF SEQ ID NOS: 84

<210> SEQ ID NO 1
<211> LENGTH: 43
<212> TYPE: DNA
<213> ORGANISM: Artificial
<220> FEATURE:
<223> OTHER INFORMATION: Synthesized primer.

<400> SEQUENCE: 1
gaaccagtga catacggatt ttcagtccgc cgttctaccg act    43

<210> SEQ ID NO 2
<211> LENGTH: 43
<212> TYPE: DNA
<213> ORGANISM: Artificial

-continued

```
<220> FEATURE:
<223> OTHER INFORMATION: Synthesized primer.

<400> SEQUENCE: 2
gaaccagtga catacggaac ctcaatccgc cgttctaccg act            43

<210> SEQ ID NO 3
<211> LENGTH: 43
<212> TYPE: DNA
<213> ORGANISM: Artificial
<220> FEATURE:
<223> OTHER INFORMATION: Synthesized primer.

<400> SEQUENCE: 3
gaaccagtga catacggatt atcagtccgc cgttctaccg act            43

<210> SEQ ID NO 4
<211> LENGTH: 43
<212> TYPE: DNA
<213> ORGANISM: Artificial
<220> FEATURE:
<223> OTHER INFORMATION: Synthesized primer.

<400> SEQUENCE: 4
gaaccagtga catacggaat gtcaatccgc cgttctaccg act            43

<210> SEQ ID NO 5
<211> LENGTH: 43
<212> TYPE: DNA
<213> ORGANISM: Artificial
<220> FEATURE:
<223> OTHER INFORMATION: Synthesized primer.

<400> SEQUENCE: 5
gaaccagtga catacggatt tccagtccgc cgttctaccg act            43

<210> SEQ ID NO 6
<211> LENGTH: 43
<212> TYPE: DNA
<213> ORGANISM: Artificial
<220> FEATURE:
<223> OTHER INFORMATION: Synthesized primer.

<400> SEQUENCE: 6
gaaccagtga catacggaac cccattccgc cgttctaccg act            43

<210> SEQ ID NO 7
<211> LENGTH: 43
<212> TYPE: DNA
<213> ORGANISM: Artificial
<220> FEATURE:
<223> OTHER INFORMATION: Synthesized primer.

<400> SEQUENCE: 7
gaaccagtga catacggatt accaatccgc cgttctaccg act            43

<210> SEQ ID NO 8
<211> LENGTH: 43
<212> TYPE: DNA
<213> ORGANISM: Artificial
<220> FEATURE:
<223> OTHER INFORMATION: Synthesized primer.

<400> SEQUENCE: 8
gaaccagtga catacggact gccagtccgc cgttctaccg act            43
```

<210> SEQ ID NO 9
<211> LENGTH: 43
<212> TYPE: DNA
<213> ORGANISM: Artificial
<220> FEATURE:
<223> OTHER INFORMATION: Synthesized primer.

<400> SEQUENCE: 9
gaaccagtga catacggatt tacagtccgc cgttctaccg act         43

<210> SEQ ID NO 10
<211> LENGTH: 43
<212> TYPE: DNA
<213> ORGANISM: Artificial
<220> FEATURE:
<223> OTHER INFORMATION: Synthesized primer.

<400> SEQUENCE: 10
gaaccagtga catacggatt cacaatccgc cgttctaccg act         43

<210> SEQ ID NO 11
<211> LENGTH: 43
<212> TYPE: DNA
<213> ORGANISM: Artificial
<220> FEATURE:
<223> OTHER INFORMATION: Synthesized primer.

<400> SEQUENCE: 11
gaaccagtga catacggatt aagagtccgc cgttctaccg act         43

<210> SEQ ID NO 12
<211> LENGTH: 43
<212> TYPE: DNA
<213> ORGANISM: Artificial
<220> FEATURE:
<223> OTHER INFORMATION: Synthesized primer.

<400> SEQUENCE: 12
gaaccagtga catacggatt gacaatccgc cgttctaccg act         43

<210> SEQ ID NO 13
<211> LENGTH: 43
<212> TYPE: DNA
<213> ORGANISM: Artificial
<220> FEATURE:
<223> OTHER INFORMATION: Synthesized primer.

<400> SEQUENCE: 13
gaaccagtga catacggatt tgcagtccgc cgttctaccg act         43

<210> SEQ ID NO 14
<211> LENGTH: 43
<212> TYPE: DNA
<213> ORGANISM: Artificial
<220> FEATURE:
<223> OTHER INFORMATION: Synthesized primer.

<400> SEQUENCE: 14
gaaccagtga catacggatc cgcagtccgc cgttctaccg act         43

<210> SEQ ID NO 15
<211> LENGTH: 43
<212> TYPE: DNA
<213> ORGANISM: Artificial
<220> FEATURE:
<223> OTHER INFORMATION: Synthesized primer.

```
<400> SEQUENCE: 15
gaaccagtga catacggatt agcagtccgc cgttctaccg act            43

<210> SEQ ID NO 16
<211> LENGTH: 43
<212> TYPE: DNA
<213> ORGANISM: Artificial
<220> FEATURE:
<223> OTHER INFORMATION: Synthesized primer.

<400> SEQUENCE: 16
gaaccagtga catacggatt ggcaatccgc cgttctaccg act            43

<210> SEQ ID NO 17
<211> LENGTH: 43
<212> TYPE: DNA
<213> ORGANISM: Artificial
<220> FEATURE:
<223> OTHER INFORMATION: Synthesized primer.

<400> SEQUENCE: 17
gaaccagtga catacggatt atgagtccgc cgttctaccg act            43

<210> SEQ ID NO 18
<211> LENGTH: 49
<212> TYPE: DNA
<213> ORGANISM: Artificial
<220> FEATURE:
<223> OTHER INFORMATION: Synthesized primer.

<400> SEQUENCE: 18
gtaatacgac tcactatagg ctctgtagtt cagtcggtag aacggcgga      49

<210> SEQ ID NO 19
<211> LENGTH: 38
<212> TYPE: DNA
<213> ORGANISM: Artificial
<220> FEATURE:
<223> OTHER INFORMATION: Synthesized primer.

<400> SEQUENCE: 19
tggcggctct gactggactc gaaccagtga catacgga                  38

<210> SEQ ID NO 20
<211> LENGTH: 22
<212> TYPE: DNA
<213> ORGANISM: Artificial
<220> FEATURE:
<223> OTHER INFORMATION: Synthesized primer.

<400> SEQUENCE: 20
ggcgtaatac gactcactat ag                                   22

<210> SEQ ID NO 21
<211> LENGTH: 20
<212> TYPE: DNA
<213> ORGANISM: Artificial
<220> FEATURE:
<223> OTHER INFORMATION: Synthesized primer.

<400> SEQUENCE: 21
tggcggctct gactggactc                                      20

<210> SEQ ID NO 22
```

```
<211> LENGTH: 5
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: formylmethionine
<220> FEATURE:
<221> NAME/KEY: MISC_FEATURE
<222> LOCATION: (5)..(5)
<223> OTHER INFORMATION: Cyclic N-alkyl amino acid
<220> FEATURE:
<221> NAME/KEY: MISC_FEATURE
<222> LOCATION: (5)..(5)
<223> OTHER INFORMATION: Cyclic N-alkyl amino acid

<400> SEQUENCE: 22

Met Lys Lys Lys Xaa
1               5

<210> SEQ ID NO 23
<211> LENGTH: 5
<212> TYPE: PRT
<213> ORGANISM: Artificial
<220> FEATURE:
<223> OTHER INFORMATION: Symthesized peptide.
<220> FEATURE:
<221> NAME/KEY: MOD_RES
<222> LOCATION: (1)..(1)
<223> OTHER INFORMATION: formylmethionine
<220> FEATURE:
<221> NAME/KEY: MISC_FEATURE
<222> LOCATION: (5)..(5)
<223> OTHER INFORMATION: Cyclic N-alkyl amino acid

<400> SEQUENCE: 23

Met Tyr Tyr Tyr Xaa
1               5

<210> SEQ ID NO 24
<211> LENGTH: 9
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: formylmethionine
<220> FEATURE:
<221> NAME/KEY: MISC_FEATURE
<222> LOCATION: (5)..(5)
<223> OTHER INFORMATION: Cyclic N-alkyl amino acid
<220> FEATURE:
<221> NAME/KEY: MISC_FEATURE
<222> LOCATION: (6)..(6)
<223> OTHER INFORMATION: Cyclic N-alkyl amino acid

<400> SEQUENCE: 24

Met Tyr Tyr Tyr Xaa Xaa Tyr Tyr Tyr
1               5

<210> SEQ ID NO 25
<211> LENGTH: 46
<212> TYPE: DNA
<213> ORGANISM: Artificial
<220> FEATURE:
<223> OTHER INFORMATION: Synthesized primer.

<400> SEQUENCE: 25
```
taatacgact cactataggg ttaactttaa caaggagaaa aacatg            46

<210> SEQ ID NO 26
<211> LENGTH: 40
<212> TYPE: DNA
<213> ORGANISM: Artificial
<220> FEATURE:
<223> OTHER INFORMATION: Synthesized primer.

<400> SEQUENCE: 26
tcgtccttgt agtcggagta gtagtacatg tttttctcct                  40

<210> SEQ ID NO 27
<211> LENGTH: 22
<212> TYPE: DNA
<213> ORGANISM: Artificial
<220> FEATURE:
<223> OTHER INFORMATION: Synthesized primer.

<400> SEQUENCE: 27
ggcgtaatac gactcactat ag                                     22

<210> SEQ ID NO 28
<211> LENGTH: 33
<212> TYPE: DNA
<213> ORGANISM: Artificial
<220> FEATURE:
<223> OTHER INFORMATION: Synthesized primer.

<400> SEQUENCE: 28
cgaagcttac ttgtcgtcgt cgtccttgta gtc                         33

<210> SEQ ID NO 29
<211> LENGTH: 37
<212> TYPE: DNA
<213> ORGANISM: Artificial
<220> FEATURE:
<223> OTHER INFORMATION: Synthesized primer.

<400> SEQUENCE: 29
ggttaacttt aacaaggaga aaacatgta ctactac                      37

<210> SEQ ID NO 30
<211> LENGTH: 40
<212> TYPE: DNA
<213> ORGANISM: Artificial
<220> FEATURE:
<223> OTHER INFORMATION: Synthesized primer.

<400> SEQUENCE: 30
tattagtagt agtacctaga agagtagtag tacatgtttt                  40

<210> SEQ ID NO 31
<211> LENGTH: 40
<212> TYPE: DNA
<213> ORGANISM: Artificial
<220> FEATURE:
<223> OTHER INFORMATION: Synthesized primer.

<400> SEQUENCE: 31
ggcgtaatac gactcactat agggttaact ttaacaagga                  40

<210> SEQ ID NO 32
<211> LENGTH: 18
<212> TYPE: DNA
<213> ORGANISM: Artificial

<220> FEATURE:
<223> OTHER INFORMATION: Synthesized primer.

<400> SEQUENCE: 32
ttattagtag tagtacct                                                 18

<210> SEQ ID NO 33
<211> LENGTH: 37
<212> TYPE: DNA
<213> ORGANISM: Artificial
<220> FEATURE:
<223> OTHER INFORMATION: Synthesized primer.

<400> SEQUENCE: 33
ggttaacttt aacaaggaga aaaacatgta gtagtag                            37

<210> SEQ ID NO 34
<211> LENGTH: 40
<212> TYPE: DNA
<213> ORGANISM: Artificial
<220> FEATURE:
<223> OTHER INFORMATION: Synthesized primer.

<400> SEQUENCE: 34
attactacta ctaccgagaa agctactact acatgttttt                         40

<210> SEQ ID NO 35
<211> LENGTH: 40
<212> TYPE: DNA
<213> ORGANISM: Artificial
<220> FEATURE:
<223> OTHER INFORMATION: Synthesized primer.

<400> SEQUENCE: 35
attactacta ctaccgagaa aactactact acatgttttt                         40

<210> SEQ ID NO 36
<211> LENGTH: 40
<212> TYPE: DNA
<213> ORGANISM: Artificial
<220> FEATURE:
<223> OTHER INFORMATION: Synthesized primer.

<400> SEQUENCE: 36
attactacta ctaccgagga aactactact acatgttttt                         40

<210> SEQ ID NO 37
<211> LENGTH: 40
<212> TYPE: DNA
<213> ORGANISM: Artificial
<220> FEATURE:
<223> OTHER INFORMATION: Synthesized primer.

<400> SEQUENCE: 37
attactacta ctaccgagga agctactact acatgttttt                         40

<210> SEQ ID NO 38
<211> LENGTH: 40
<212> TYPE: DNA
<213> ORGANISM: Artificial
<220> FEATURE:
<223> OTHER INFORMATION: Synthesized primer.

<400> SEQUENCE: 38
attactacta ctaccgaaaa agctactact acatgttttt                         40

<210> SEQ ID NO 39
<211> LENGTH: 19
<212> TYPE: DNA
<213> ORGANISM: Artificial
<220> FEATURE:
<223> OTHER INFORMATION: Synthesized primer.

<400> SEQUENCE: 39
ttattactac tactaccga                                                19

<210> SEQ ID NO 40
<211> LENGTH: 40
<212> TYPE: DNA
<213> ORGANISM: Artificial
<220> FEATURE:
<223> OTHER INFORMATION: Synthesized primer.

<400> SEQUENCE: 40
ttactactac taccgaggaa aaagctacta ctacatgttt                          40

<210> SEQ ID NO 41
<211> LENGTH: 40
<212> TYPE: DNA
<213> ORGANISM: Artificial
<220> FEATURE:
<223> OTHER INFORMATION: Synthesized primer.

<400> SEQUENCE: 41
ttactactac taccgaggag aaaactacta ctacatgttt                          40

<210> SEQ ID NO 42
<211> LENGTH: 40
<212> TYPE: DNA
<213> ORGANISM: Artificial
<220> FEATURE:
<223> OTHER INFORMATION: Synthesized primer.

<400> SEQUENCE: 42
ttactactac taccgaggag aaagctacta ctacatgttt                          40

<210> SEQ ID NO 43
<211> LENGTH: 40
<212> TYPE: DNA
<213> ORGANISM: Artificial
<220> FEATURE:
<223> OTHER INFORMATION: Synthesized primer.

<400> SEQUENCE: 43
ttactactac taccgagaaa aaagctacta ctacatgttt                          40

<210> SEQ ID NO 44
<211> LENGTH: 40
<212> TYPE: DNA
<213> ORGANISM: Artificial
<220> FEATURE:
<223> OTHER INFORMATION: Synthesized primer.

<400> SEQUENCE: 44
tactactact accgaggaga aaaaagctac tactacatgt                          40

<210> SEQ ID NO 45
<211> LENGTH: 40
<212> TYPE: DNA
<213> ORGANISM: Artificial
<220> FEATURE:
<223> OTHER INFORMATION: Synthesized primer.

<400> SEQUENCE: 45
tactactact accgatgacg acaatactac tactacatgt                                40

<210> SEQ ID NO 46
<211> LENGTH: 40
<212> TYPE: DNA
<213> ORGANISM: Artificial
<220> FEATURE:
<223> OTHER INFORMATION: Synthesized primer.

<400> SEQUENCE: 46
tactactact accgagcaat agtaacctac tactacatgt                                40

<210> SEQ ID NO 47
<211> LENGTH: 40
<212> TYPE: DNA
<213> ORGANISM: Artificial
<220> FEATURE:
<223> OTHER INFORMATION: Synthesized primer.

<400> SEQUENCE: 47
tactactact accgatcacc actattctac tactacatgt                                40

<210> SEQ ID NO 48
<211> LENGTH: 44
<212> TYPE: DNA
<213> ORGANISM: Artificial
<220> FEATURE:
<223> OTHER INFORMATION: Synthesized primer.

<400> SEQUENCE: 48
atactaatac gactcactat aggattaagg aggtgatatt tatg                           44

<210> SEQ ID NO 49
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 49
ccgccgccgc cggcagnnan nanncataaa tatcacctcc                                40

<210> SEQ ID NO 50
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)

<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 50
ctgctgctgc tggcagnnan nanncataaa tatcacctcc                40

<210> SEQ ID NO 51
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 51
ctcctcctcc tcgcagnnan nanncataaa tatcacctcc                40

<210> SEQ ID NO 52
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 52
cttcttcttc ttgcagnnan nanncataaa tatcacctcc                40

<210> SEQ ID NO 53
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 53
catcatcatc atgcagnnan nanncataaa tatcacctcc        40

<210> SEQ ID NO 54
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 54
ccaccaccac cagcagnnan nanncataaa tatcacctcc        40

<210> SEQ ID NO 55
<211> LENGTH: 39
<212> TYPE: DNA
<213> ORGANISM: Artificial
<220> FEATURE:
<223> OTHER INFORMATION: Synthesized primer.

<400> SEQUENCE: 55
cccgcctccc gcccccgtc ctaccgccgc cgccggcag        39

<210> SEQ ID NO 56
<211> LENGTH: 39
<212> TYPE: DNA
<213> ORGANISM: Artificial
<220> FEATURE:
<223> OTHER INFORMATION: Synthesized primer.

<400> SEQUENCE: 56
cccgcctccc gcccccgtc ctactgctgc tgctggcag        39

<210> SEQ ID NO 57
<211> LENGTH: 39
<212> TYPE: DNA
<213> ORGANISM: Artificial
<220> FEATURE:
<223> OTHER INFORMATION: Synthesized primer.

<400> SEQUENCE: 57
cccgcctccc gcccccgtc ctactcctcc tcctcgcag        39

<210> SEQ ID NO 58
<211> LENGTH: 39
<212> TYPE: DNA
<213> ORGANISM: Artificial
<220> FEATURE:
<223> OTHER INFORMATION: Synthesized primer.

<400> SEQUENCE: 58
cccgcctccc gcccccgtc ctacttcttc ttcttgcag        39

<210> SEQ ID NO 59
<211> LENGTH: 39
<212> TYPE: DNA

```
<213> ORGANISM: Artificial
<220> FEATURE:
<223> OTHER INFORMATION: Synthesized primer.

<400> SEQUENCE: 59
cccgcctccc gcccccgtc ctacatcatc atcatgcag                              39

<210> SEQ ID NO 60
<211> LENGTH: 39
<212> TYPE: DNA
<213> ORGANISM: Artificial
<220> FEATURE:
<223> OTHER INFORMATION: Synthesized primer.

<400> SEQUENCE: 60
cccgcctccc gcccccgtc ctaccaccac caccagcag                              39

<210> SEQ ID NO 61
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 61
catcatcatc atccagnnan nanncataaa tatcacctcc                            40

<210> SEQ ID NO 62
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 62
ctacatcatc atccagnnan nanncataaa tatcacctcc                            40

<210> SEQ ID NO 63
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
```

```
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 63
ctactacatc atccagnnan nanncataaa tatcacctcc                              40

<210> SEQ ID NO 64
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 64
ctactactac atccagnnan nanncataaa tatcacctcc                              40

<210> SEQ ID NO 65
<211> LENGTH: 40
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 65
ctactactac taccagnnan nanncataaa tatcacctcc                              40

<210> SEQ ID NO 66
<211> LENGTH: 39
<212> TYPE: DNA
<213> ORGANISM: Artificial
<220> FEATURE:
<223> OTHER INFORMATION: Synthesized primer.

<400> SEQUENCE: 66
cccgcctccc gcccccgtc ctacatcatc atcatccag                               39

<210> SEQ ID NO 67
<211> LENGTH: 39
<212> TYPE: DNA
<213> ORGANISM: Artificial
<220> FEATURE:
```

<223> OTHER INFORMATION: Synthesized primer.

<400> SEQUENCE: 67
cccgcctccc gcccccgtc ctactacatc atcatccag          39

<210> SEQ ID NO 68
<211> LENGTH: 39
<212> TYPE: DNA
<213> ORGANISM: Artificial
<220> FEATURE:
<223> OTHER INFORMATION: Synthesized primer.

<400> SEQUENCE: 68
cccgcctccc gcccccgtc ctactactac atcatccag          39

<210> SEQ ID NO 69
<211> LENGTH: 39
<212> TYPE: DNA
<213> ORGANISM: Artificial
<220> FEATURE:
<223> OTHER INFORMATION: Synthesized primer.

<400> SEQUENCE: 69
cccgcctccc gcccccgtc ctactactac tacatccag          39

<210> SEQ ID NO 70
<211> LENGTH: 39
<212> TYPE: DNA
<213> ORGANISM: Artificial
<220> FEATURE:
<223> OTHER INFORMATION: Synthesized primer.

<400> SEQUENCE: 70
cccgcctccc gcccccgtc ctactactac tactaccag          39

<210> SEQ ID NO 71
<211> LENGTH: 59
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 71
tacatcatca tcatccagnn annannanna nnannannan ncataaatat cacctcctt    59

<210> SEQ ID NO 72
<211> LENGTH: 18
<212> TYPE: DNA
<213> ORGANISM: Artificial
<220> FEATURE:
<223> OTHER INFORMATION: Synthesized primer.

<400> SEQUENCE: 72
taccgccgcc gccggcag                                                 18

<210> SEQ ID NO 73
<211> LENGTH: 18
<212> TYPE: DNA
<213> ORGANISM: Artificial
<220> FEATURE:
<223> OTHER INFORMATION: Synthesized primer.

<400> SEQUENCE: 73
tactgctgct gctggcag                                                 18

<210> SEQ ID NO 74
<211> LENGTH: 18
<212> TYPE: DNA
<213> ORGANISM: Artificial
<220> FEATURE:
<223> OTHER INFORMATION: Synthesized primer.

<400> SEQUENCE: 74
tactcctcct cctcgcag                                                 18

<210> SEQ ID NO 75
<211> LENGTH: 18
<212> TYPE: DNA
<213> ORGANISM: Artificial
<220> FEATURE:
<223> OTHER INFORMATION: Synthesized primer.

<400> SEQUENCE: 75
tacttcttct tcttgcag                                                 18

<210> SEQ ID NO 76
<211> LENGTH: 18
<212> TYPE: DNA
<213> ORGANISM: Artificial
<220> FEATURE:
<223> OTHER INFORMATION: Synthesized primer.

<400> SEQUENCE: 76
tacatcatca tcatgcag                                                 18

<210> SEQ ID NO 77
<211> LENGTH: 18
<212> TYPE: DNA
<213> ORGANISM: Artificial
<220> FEATURE:
<223> OTHER INFORMATION: Synthesized primer.

<400> SEQUENCE: 77
taccaccacc accagcag                                                 18

```
<210> SEQ ID NO 78
<211> LENGTH: 18
<212> TYPE: DNA
<213> ORGANISM: Artificial
<220> FEATURE:
<223> OTHER INFORMATION: Synthesized primer.

<400> SEQUENCE: 78
taccgccgcc gccggcag                                                 18

<210> SEQ ID NO 79
<211> LENGTH: 18
<212> TYPE: DNA
<213> ORGANISM: Artificial
<220> FEATURE:
<223> OTHER INFORMATION: Synthesized primer.

<400> SEQUENCE: 79
tacatcatca tcatccag                                                 18

<210> SEQ ID NO 80
<211> LENGTH: 18
<212> TYPE: DNA
<213> ORGANISM: Artificial
<220> FEATURE:
<223> OTHER INFORMATION: Synthesized primer.

<400> SEQUENCE: 80
tactacatca tcatccag                                                 18

<210> SEQ ID NO 81
<211> LENGTH: 18
<212> TYPE: DNA
<213> ORGANISM: Artificial
<220> FEATURE:
<223> OTHER INFORMATION: Synthesized primer.

<400> SEQUENCE: 81
tactactaca tcatccag                                                 18

<210> SEQ ID NO 82
<211> LENGTH: 18
<212> TYPE: DNA
<213> ORGANISM: Artificial
<220> FEATURE:
<223> OTHER INFORMATION: Synthesized primer.

<400> SEQUENCE: 82
tactactact acatccag                                                 18

<210> SEQ ID NO 83
<211> LENGTH: 18
<212> TYPE: DNA
<213> ORGANISM: Artificial
<220> FEATURE:
<223> OTHER INFORMATION: Synthesized primer.

<400> SEQUENCE: 83
tactactact actaccag                                                 18

<210> SEQ ID NO 84
<211> LENGTH: 76
<212> TYPE: RNA
<213> ORGANISM: Artificial
<220> FEATURE:
<223> OTHER INFORMATION: Synthesized tRNA.
```

```
<220> FEATURE:
<221> NAME/KEY: misc_feature
<222> LOCATION: (32)..(38)
<223> OTHER INFORMATION: n is a, c, g or u and nucleotides at position
      32-38 are anticodon loop.

<400> SEQUENCE: 84
ggcucuguag uucagucggu agaacggcgg annnnnnnuc cguaugucac ugguucgagu      60
ccagucagag ccgcca                                                     76
```

METHOD FOR PRODUCING PEPTIDE LIBRARY, PEPTIDE LIBRARY, AND SCREENING METHOD

REFERENCE TO A SEQUENCE LISTING SUBMITTED VIA EFS-WEB

The content of the ASCII text file of the sequence listing named "20160307_034574_007US1_subseq" which is 19.0 kb in size was created on Mar. 7, 2016 and electronically submitted via EFS-Web herewith the application is incorporated herein by reference in its entirety.

TECHNICAL FIELD

The present invention relates to a method for producing a peptide library that makes use of codon reassignment, and the like.

BACKGROUND ART

Peptide selection using in vitro display method such as ribosome display (Reference Documents 1 and 2) or mRNA display (Reference Documents 3 and 4) is a leading method for searching novel functional peptides from a highly diverse peptide library. A library comprised of peptides having a cyclic structure or peptides having an N-alkylated peptide backbone in in vitro display method becomes also useful for screening of a drug candidate targeting an intracellular disease-associated molecule or a molecule having protease activity because the peptides obtain enhanced resistance against proteolysis, cell membrane permeability, and conformational rigidity.

It has so far been shown in fact that peptides macrocyclized after translation is used for in vitro peptide selection (Reference Documents 6 to 10) and in some cases, selected cyclic peptides have higher affinity for a target protein than a linear peptide corresponding thereto (Reference Documents 6, 8, and 10). With respect to N-alkylation of a peptide backbone, ribosomal synthesis of N-methyl peptide and peptoid has been developed in order to enhance membrane permeability of peptides or resistance against proteolysis (Reference Documents 11 to 16).

Further, a partially N-methylated macrocyclic peptide library constructed in a ribosomal translation system is used for selecting novel macrocyclic n-methyl peptides by using mRNA display (Reference Document 17). In the macrocyclic N-methyl peptides, both N-methylation and a cyclic structure are important for resistance against proteolysis (Reference Document 17). Excellent pharmacological properties produced by the cyclic structure and N-alkyl peptide structure show that cyclic N-alkyl amino acids (CNA) will be a useful building block for simultaneously enhancing cell permeability, resistance against proteolysis, and conformational rigidity.

Adaptability of CNA to a ribosomal translation system is important for using CNA-containing ribosomally synthesized peptides for selection. In classical in vitro nonsense suppression using a translation system with a cell extract, a ribosomal translation mechanism allows some CNAs (2, 3, and 4 in FIG. 1a) to serve as a substrate (Reference Documents 18 to 20). It has been shown that CNAs 7, 8, and 22 of FIG. 1a) charged onto tRNA by a wild type prolyl-tRNA synthetase (ProRS) are incorporated into ribosome in vivo (Reference Documents 21 to 23). These methods however fail to provide a uniform translation product with good reproducibility because they compete with termination of translation by an endogenous release factor-1 (RF1) or incorporation of natural proline. Therefore, these methods cannot be used for preparation of a peptide library including non-proteinogenic CNA for peptide selection.

Two groups have studied incorporation of non-proteinogenic CNA into ribosome by using a reconstituted cell-free translation system (Reference Documents 24 to 33). Forster, et al. have reported (Non-patent Document 1) that 3-trans-hydroxyproline (3 of FIG. 1A) chemoenzymatically charged onto tRNA is incorporated in a peptide at an efficiency equal to that of alanine or phenylalanine (Non-patent Document 1). Forster, et al. have suggested in addition that CNAs (proline and 3-trans-hydroxyproline) are likely to be incorporated into a peptide not by a linear N-alkyl amino acid (N-methyl amino acid and N-butyl amino acid) but by a translation apparatus. Foster, et al. however have actually shown incorporation of only one 3-trans-hydroxyproline into a peptide but they do not perform ribosomal translation of a peptide containing a plurality of non-proteinogenic CNA-tRNAs (Non-patent Document 2). This is presumed to result from difficulty in chemoenzymatic acylation of tRNA (Reference Documents 34 to 37).

Szostak, et al. have shown that four CNAs including thiazolidine-2-carboxylic acids (6 of FIG. 1A), thiazolidine-4-carboxylic acid (5 of FIG. 1A), and 3,4-dehydroproline (22 of FIG. 1A) serve as a substrate of ProRS and a translation apparatus (Non-patent Documents 3 and 4). The thiazolidine-4-carboxylic acid is used as a building block in mRNA display selection, showing usefulness of non-proteinogenic CNA in in vitro peptide selection (Reference Document 10). In tRNA acylation method using this ProRS catalyst, however, a plurality of different CNAs cannot be simultaneously incorporated into different codons because CNA is incorporated only into the codon representing proline. Further, some CNAs do not serve as a substrate for aminoacyl tRNA synthase (aaRS) (Reference Document 38) so that translation using CNAs is limited to the number of CNAs having good affinity for aaRS.

Thus, the study by two groups has revealed that a limited kind of CNAs is incorporated into a peptide and the number of the CNAs incorporated into the peptide is one, but due to limitation in the tRNA acylation method employed, there has been no report on comprehensive adaptability screening or incorporation of many different CNAs in a plurality of sites.

CITATION LIST

Non-Patent Documents

Non-patent Document 1: Zhang, B. et al. J. Am. Chem. Soc. 129, 11316-11317 (2007).
Non-patent Document 2: Forster, A. C. Biotechnol J 7, 835-845 (2012). Non-patent Document 3: Hartman, M. C., et al. Proc. Natl. Acad. Sci. USA 103, 4356-4361 (2006).
Non-patent Document 4: Hartman, M. C., et al. PLoS One 2, e972 (2007).

DISCLOSURE OF THE INVENTION

Problem to be Solved by the Invention

An object of the present invention is to provide a method for producing a peptide library capable of incorporating an arbitrary number of arbitrary proteinogenic amino acids and/or non-proteinogenic amino acids in arbitrary sites, respectively, and the like.

Means for Solving the Problem

The present inventors have confirmed that a desired number of desired non-proteinogenic CNAs can be incorporated into a peptide by re-assigning respectively different non-proteinogenic CNAs to codons represented by $N_1N_2N_3$ ($N_1$, $N_2$, and $N_3$ are each independently selected from adenine (A), guanine (G), cytosine (C), and uracil (U) and an arbitrary amino acid is reassigned to each $N_1N_2N_3$), respectively, during codon reassignment; charging 16 tRNAs having anticodons to the above-mentioned codons with the non-proteinogenic CNAs corresponding thereto, respectively; and translating mRNA containing a plurality of $N_1N_2N_3$ codons by using them.

In addition, it has been confirmed that a desired number of desired amino acids are incorporated into a peptide also by assigning not only non-proteinogenic CNAs but also non-proteinogenic amino acids or proteinogenic amino acids each different from a natural one to 16 kinds of $N_1N_2N_3$ codons, charging 16 tRNAs having anticodons to the above-mentioned codons with amino acids corresponding thereto, and translating mRNA containing a plurality of $N_1N_2N_3$ codons.

Further, it has been confirmed that when non-proteinogenic amino acids or proteinogenic amino acids each different from a natural one are assigned to 16 kinds of $N_1N_2N_3$ codons, respectively, the same tRNA can be used as all the elongator tRNAs, leading to completion of the present invention.

The present invention relates to:

[1] a translation system including only the following (a) and (b) as a tRNA:
(a) an initiator tRNA; and
(b) elongator tRNAs having base sequences 85% or more identical to one another in total length, respectively;

[2] the translation system as described above in [1], wherein the elongator tRNAs (b) have base sequences identical to one another except for anticodon loop;

[3] the translation system as described above in [1] or [2], capable of producing a peptide library including $1 \times 10^6$ or more respectively different peptides;

[4] a method for producing a peptide library including $1 \times 10^6$ or more peptides containing amino acids encoded by $N_1N_2N_3$, including:
a step of preparing an mRNA library including mRNAs which encode the peptides of the peptide library, respectively, and each contain a plurality of $N_1N_2N_3$s; and
a step of translating each of the mRNAs of the mRNA library in a cell-free translation system added with a tRNA containing an anticodon to any of $N_1N_2N_3$ codons and charged with an amino acid corresponding to the codon (wherein $N_1$, $N_2$, and $N_3$ are each independently selected from adenine (A), guanine (G), cytosine (C), and uracil (U) and an arbitrary amino acid is reassigned to each $N_1N_2N_3$);

[5] the method as described above in [4], wherein each of the mRNAs included in the mRNA library is represented by the following formula (I):

$$X_1-(N_1N_2N_3)n-X_2 \quad (I)$$

[wherein, $X_1$ and $X_2$ each represent an mRNA encoding a peptide composed of an arbitrary number of amino acids, and n stands for an arbitrary integer selected from 4 to 20];

[6] a method for producing a peptide-mRNA complex library including $1 \times 10^6$ or more kinds of complexes between a peptide containing an amino acid encoded by $N_1N_2N_3$ and an mRNA encoding the peptide, including:
a step of preparing a puromycin-bound mRNA library which contains an mRNA encoding a peptide portion of the peptide-mRNA complex library, includes, in the mRNA portion, a plurality of $N_1N_2N_3$s, and has puromycin bound to a downstream region of ORF in the mRNA; and
a step of translating each of the mRNA of the puromycin-bound mRNA library in a cell-free translation system added with a tRNA containing an anticodon to any of $N_1N_2N_3$ codons and charged with an amino acid corresponding the codon, and thereby producing a peptide-mRNA complex library (wherein $N_1$, $N_2$, and $N_3$ are each independently selected from adenine (A), guanine (G), cytosine (C), and uracil (U) and an arbitrary amino acid is reassigned to each $N_1N_2N_3$).

[7] the method as described above in [6], wherein each of the mRNAs included in the puromycin-bound mRNA library is represented by the following formula (I):

$$X_1-(N_1N_2N_3)n-X_2 \quad (I)$$

wherein, $X_1$ and $X_2$ each represent an mRNA encoding a peptide having an arbitrary number of amino acids and n stands for an arbitrary integer selected from 4 to 20;

[8] the method as described above in any one of [4] to [7], wherein the $N_3$ is either the following (i) or (ii) in one translation system:
(i) cytosine (C) or uracil (U); and
(ii) adenine (A) or guanine (G);

[9] the method as described above in any one of [4] to [8], wherein 16 kinds of the $N_1N_2N_3$s are present in one translation system;

[10] the method as described above in any one of [4] to [9], wherein the amino acids encoded by $N_1N_2N_3$ contain a non-proteinogenic amino acid;

[11] the method as described above in any one [4] to [9], wherein the amino acids encoded by $N_1N_2N_3$ are all non-proteinogenic amino acids;

[12] the method as described above in any one of [4] to [11], wherein, of the tRNAs charged with an amino acid corresponding to the $N_1N_2N_3$ codon, elongator tRNAs have base sequences having 85% or more sequence homology with each other, respectively;

[13] the method as described above in any one of [4] to [11], wherein, of the tRNAs charged with an amino acid corresponding to the $N_1N_2N_3$ codon, elongator tRNAs have RNA sequences identical to each other except for an anticodon loop, respectively;

[14] the method as described above in [4] to [13], further including, after the translation step, a peptide macrocyclization step;

[15] a library, including $1 \times 10^6$ or more kinds of peptides encoded by an mRNA library represented by the following formula (I):

$$X_1-(N_1N_2N_3)n-X_2 \quad (I)$$

[wherein, $N_1$, $N_2$, and $N_3$ are each independently selected from adenine (A), guanine (G), cytosine (C), and uracil (U); an arbitrary amino acid is reassigned to each $N_1N_2N_3$; $X_1$ and $X_2$ each represent an mRNA encoding a peptide having an arbitrary number of amino acids; and n stands for an arbitrary integer selected from 4 to 20];

[16] a library, including 1×10⁶ or more kinds of peptides encoded by an mRNA library represented by the following formula (I), the peptides each constituting a complex with an mRNA encoding the peptide:

$$X_1-(N_1N_2N_3)n\text{-}X_2 \qquad (I)$$

[wherein, $N_1$, $N_2$, and $N_3$ are each independently selected from adenine (A), guanine (G), cytosine (C), and uracil (U); an arbitrary amino acid is reassigned to each $N_1N_2N_3$; $X_1$ and $X_2$ each represent an mRNA encoding a peptide having an arbitrary number of amino acids; and n stands for an arbitrary integer selected from 4 to 20];

[17] the peptide library as described above in [15] or [16], wherein the $N_3$ is either the following (i) or (ii) in one translation system:
  (i) cytosine (C) or uracil (U); or
  (ii) adenine (A) or guanine (G);

[18] the peptide library as described above in any one of [15] to [17], wherein the peptides constituting the library each form a macrocycle;

[19] a screening method for identifying a peptide to be bound to a target substance, including:
  a step of bringing the peptide library produced by the method as described above in any one of [4] to [14] or the peptide library as described above in any one of [15] to [18] into contact with the target substance, followed by incubation; and
  a step of selecting the peptide bound to the target substance;

[20] a screening method for identifying a peptide to be bound to a target substance, including:
  a step of subjecting the peptide-mRNA complex library produced by the method as described above in any one of [6] to [14] or the peptide-mRNA complex library as described above in any one of [16] to [18] to a reverse transcription reaction to obtain a peptide-DNA complex library;
  a step of bringing the peptide-DNA complex library into contact with the target substance, followed by incubation;
  a step of selecting a peptide-DNA complex group bound to the target substance;
  a step of amplifying DNA of the selected peptide-DNA complex group by PCR; and
  a step of transcribing the amplified DNA to produce an mRNA library, binding puromycin to a downstream region of ORF in the mRNA to produce a puromycin-bound mRNA library, and translating it to produce a peptide-mRNA complex library;
  wherein the steps from the reverse transcription reaction to the production of the peptide-mRNA complex library is repeated twice or more to select a peptide having high affinity for the target substance.

Effect of the Invention

According to the method of the present invention, a peptide library having sufficient diversity can be produced by incorporating an arbitrary number of arbitrary proteinogenic amino acids and/or non-proteinogenic amino acids in arbitrary sites, respectively. Such a peptide library is useful for selecting a drug candidate peptide that binds to a disease-associated target molecule and can also be used for various in vitro display methods.

A peptide library obtained using an amino acid having a cyclic structure or an N-alkyl amino acid as the non-proteinogenic amino acid has enhanced resistance against proteolysis, cell membrane permeability, and conformational rigidity. Conventional peptide libraries have difficulty in targeting a molecule such as an intracellular molecule or a molecule having protease activity but the above peptide library is also useful for screening of a drug candidate that targets such a molecule.

Further, according to the method of the present invention, elongator tRNAs having sequences identical to each other except for an anticodon loop can be used for any amino acids in a translation system for expressing a peptide library so that tRNAs have uniform reactivity and predetermined peptides can be obtained with good reproducibility.

BRIEF DESCRIPTION OF THE DRAWINGS

FIG. 1 relates to DNA programmed synthesis of N-alkyl polycyclic peptidomimetics by codon reassignment. FIG. 1A shows respective chemical structures of CNAs used for experiment. 1: L-proline; 2: L-pipecolic acid; 3: trans-4-hydroxy-L-proline; 4: cis-4-hydroxy-L-proline; 5: thiazolidine-4-carboxylic acid; 6: thiazolidine-2-carboxylic acid; 7: cis-4-fluoro-L-proline; 8: trans-4-fluoro-L-proline; 9: 4,4-difluoro-L-proline; 10: 3,3-dimethyl-L-proline; 11: 1,2,3,4-tetrahydroisoquinoline-3-carboxylic acid; 12: 7-hydroxy-1,2,3,4-tetrahydroisoquinoline-3-carboxylic acid; 13: cis-4-phenyl-L-proline; 14: trans-4-phenyl-L-proline; 15: 2-tryptoline-3-carboxylic acid; 16: O-benzyl-trans-4-hydroxy-L-proline; 17: cis-3-phenyl-L-proline; 18: 4-hydroxy-L-pipecolic acid; 19: 4-oxo-L-proline; 20: (2S,3aS,7aS)-2,3,3a,4,5,6,7,7a-octahydroindole-2-carboxylic acid; 21: (1R,3S,4S)-2-azabicyclo[2.2.1]heptane-3-carboxylic acid; and 22: 3,4-dehydro-L-proline.

FIG. 1B shows a process of synthesizing, using a template mRNA, a library of complete N-alkyl polycyclic peptidomimetics displayed on their mRNAs via a puromycin (Pu)-DNA linker by using various cyclic N-alkylaminoacyl (CNA)-tRNAs in the TRAP system. In the TRAP system, N-alkyl polycyclic peptidomimetics translated from mRNA or DNA are voluntarily displayed on mRNAs encoding them, respectively.

FIG. 1C shows the results of measuring aminoacylation of microhelix RNA under optimum conditions by acid urea PAGE. CNAs 12, 15, and 17 were charged onto microhelix RNA by using enhanced-flexizyme (eFx) and a CNA cyanomethyl ester corresponding thereto, while the other CNAs were charged onto microhelix RNA by using dinitro-flexizyme (dFx) and CNA 3,5-dinitrobenzyl ester corresponding thereto.

FIG. 2 shows the design and results of an experiment for incorporating CNA in only one site of a peptide. FIG. 2A shows sequences of mRNA1 and Peptide 1 encoded thereby. CNA was assigned to the empty UCC codon.

FIG. 2D shows, on the lower side thereof, the results of MALDI-TOF MS analysis of Peptide 2 containing CNA. C and O represent calculated molecular mass and observed molecular mass of a monovalent ion [M+H]⁺, respectively. An asterisk (*) and a dagger (†) represent peaks of a full-length peptide having CNA and an incomplete-length peptide, respectively.

FIG. 2E shows, on the lower side thereof, the results of MALDI-TOF MS analysis of Peptide 3 containing CNA. C and O represent calculated molecular mass and observed molecular mass of a monovalent ion [M+H]⁺, respectively. An asterisk (*) and a dagger (†) represent peaks of a peptide having two CNAs and a peptide having one CNA, respectively.

FIG. 3 shows codon reassignment for synthesis of bis-N-alkyl bicyclic peptides by DNA programming.

FIG. 3D is a diagram for explaining misreading of the NNU codon which may occur in a G-U base pair between mRNA and near cognate tRNA thereof. What is most concerning is misreading of the first and second bases of the codon as a G-U pair instead of correct reading of it as an A-U pair or G-C pair. A correctly read NNU codon-anticodon pair is shown in the codon table, while a codon-anticodon pair misread as a G-U pair is shown outside the codon table. A thick arrow shows the possibility of misreading of an NNU codon by near-cognate tRNA. In codon reassignment, 16 NNU codons were classified into four groups so that each group included four NNU near-cognate codons and it was confirmed whether 16 NNU codons were read correctly without misreading by near-cognate codons.

FIG. 4 shows codon reassignment for expression of tris-N-alkyl tricyclic peptides by DNA programming. FIG. 4A shows template mRNAs 10 to 13 and bis-N-alkyl bicyclic peptides 10 to 13 encoded thereby.

FIG. 4B shows MALDI-TOF-MS spectra and the structure of tris-N-alkyl tricyclic peptides. Calculated molecular mass (C) and observed molecular mass (O) of a monovalent ion [M+H]⁺ are shown in each spectrum. An asterisk (*) represents a peak corresponding to each of the tris-N-alkyl tricyclic peptides.

FIG. 5 shows codon reassignment for expression of tetra-N-alkyl tetracyclic peptides by DNA programming. FIG. 5A shows respective sequences of template mRNAs 14 to 17 and bis-N-alkyl bicyclic peptides 14 to 17 encoded thereby.

FIG. 5B shows a reprogrammed genetic code for expression of tetra-N-alkyl tetracyclic peptides by DNA programming. 16 NNU codons were all assigned to 16 different CNAs, respectively.

FIG. 5C shows MALDI-TOF-MS spectra and the structures of tetra-N-alkyl tetracyclic peptides. Calculated molecular mass (C) and observed molecular mass (0) of a monovalent ion [M+H]⁺ are shown in each spectrum. An asterisk (*) represents a peak corresponding to each of the tetra-N-alkyl tetracyclic peptides.

FIGS. 6A to C shows optimization of a spacer sequence in a random NNU mRNA library used in TRAP display, performed making use of streptavidin pull-down assay. FIG. 6A shows the outline of streptavidin pull-down assay of a peptide-mRNA/cDNA complex. In TRAP system, an expressed peptide t is displayed, via a puromycin DNA linker, on the mRNA voluntarily encoding itself in a translation system. Since the peptide contains biocytin ($^{Biot}$K), the mRNA on which the peptide is displayed can be separated from an mRNA on which no peptide is displayed by beads having streptavidin immobilized thereon and quantitatively determined by real-time PCR.

FIG. 6B shows, on the upper side thereof, the respective sequences of the mRNA library and the peptide library used for optimization of the spacer sequence. The UGC codon was reassigned to $^{Biot}$K. The region of the mRNA shown with a thick letter is a spacer. The empty UAG codon for tethering a ribosome and increasing a transfer efficiency of the peptide to puromycin is underlined.

FIG. 6C shows optimization of a distance between the first empty UAG codon and the puromycin DNA linker annealing region, performed by making use of streptavidin pull down assay. It shows, on the upper side thereof, the respective sequences of the mRNA library and the peptide library used for optimization. The UGG codon was reassigned to biocytin ($^{Biot}$K). The first empty UAG codon for tethering a ribosome and increasing a transfer efficiency of the peptide to puromycin is underlined. The puromycin DNA linker annealing region is shown in italics. Xaa represents a random proteinogenic amino acid. Comparison in display efficiency among mRNA libraries having different spacer sequences is shown on the lower side.

FIG. 7 shows a display efficiency of complete N-alkyl polycyclic peptidomimetics in TRAP display, measured using streptavidin pull-down assay. FIG. 7A is a schematic view of streptavidin pull-down of a peptide-mRNA/cDNA complex. In the TRAP system, an expressed peptide is voluntarily displayed, via a pu-DNA linker, on the mRNA encoding it, in a translation system. By using streptavidin (StAv) immobilized beads, the mRNA on which the peptide (N-biotinylated phenylalanine $^{Biot}$F) encoded thereby was displayed was separated from the mRNA on which the peptide was not displayed and was quantitatively determined by real time PCR.

FIG. 8 shows MALDI TOF MS spectra of synthesized peptides obtained by aminoacylating all the tRNAs corresponding to 16 NNU codons and AUG codons by using Flexizyme, adding them, together with a similarly aminoacylated initiator tRNA, to a cell-free translation system but adding none of an aminoacyl tRNA synthase, a wild type tRNA, and a free amino acid instead, and carrying out peptide translation.

MODE FOR CARRYING OUT THE INVENTION

Production Method of Peptide Library

Figure 2B:
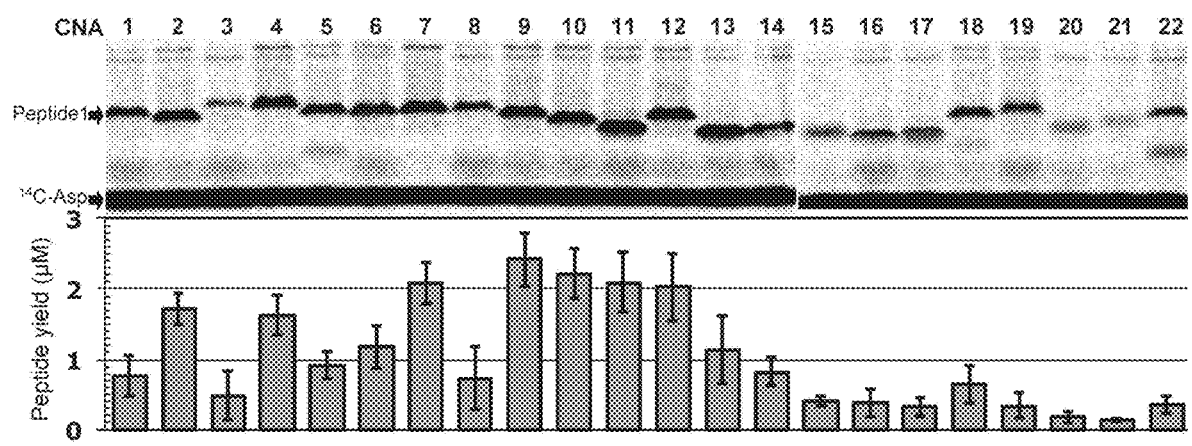
FIG. 2B shows the results of Tricine-SDS-PAGE analysis of a peptide expressed after labeled with [¹⁴C]-Asp. The peptide was synthesized in the presence of 100 μM of cyclic N-alkylaminoacyl-tRNA$^{Asn\text{-}E2}$ (GGA) prepared using Flexizyme. A production efficiency of each peptide based on a radioisotope count is shown in a lower graph. Error bars represent a standard deviation calculated based on an experiment in triplicate.

In one mode, a method for producing a peptide library according to the present invention is a method for producing a peptide library having $1 \times 10^6$ or more peptides containing an amino acid encoded by $N_1N_2N_3$, which includes:

a step of preparing an mRNA library including mRNAs which encode the peptides of the peptide library, respectively, and each contain a plurality of $N_1N_2N_3$s; and a step of translating each of the mRNAs of the mRNA library in a cell-free translation system added with a tRNA containing an anticodon to any of $N_1N_2N_3$ codons and charged with an amino acid corresponding to the codon.

The term "$N_1N_2N_3$" as used herein means a codon specifying an amino acid and $N_1$, $N_2$, and $N_3$ are each independently selected from adenine (A), guanine (G), cytosine (C), and uracil (U). One mRNA contains a plurality of $N_1N_2N_3$, but $N_1$, $N_2$, and $N_3$ are each independently selected.

For example, when an mRNA contains —$N_1N_2N_3$-$N_1N_2N_3$—, two $N_1$s, $N_2$s, or $N_3$s may be the same or different.

In one translation system, $N_3$ of $N_1N_2N_3$ may be either the following (i) or (ii).

(i) cytosine (C) or uracil (U), and
(ii) adenine (A) or guanine (G).

This means that in a certain translation system, only $N_1N_2C$ or $N_1N_2U$ is present. Only $N_1N_2C$ may be present, only $N_1N_2U$ may be present, or a mixture of $N_1N_2C$ and $N_1N_2U$ may be present.

In another translation system, only $N_1N_2A$ or $N_1N_2G$ is present. Only $N_1N_2A$ may be present, only $N_1N_2G$ may be present, or a mixture of $N_1N_2A$ and $N_1N_2G$ may be present.

In the above case (i) or (ii), there are preferably 16 codons each represented by $N_1N_2N_3$ in one translation system. Between tRNA and mRNA, the third base is allowed to be a G-U pair so that correct translation by assigning different amino acids to UUU and UUC cannot be performed. In the case (i), either C or U is preferably selected as $N_3$ for 16 kinds of $N_1N_2$, and similarly, in the case (ii), either A or G is preferably selected as $N_3$ for 16 kinds of $N_1N_2$.

Described specifically, in one translation system, 16 kinds of $N_1N_2N_3$ represented by $N_1N_2U$ may be used, 16 kinds of $N_1N_2N_3$ represented by $N_1N_2C$ may be used, or 16 kinds of $N_1N_2N_3$ represented by $N_1N_2U$ and $N_1N_2C$ may be used; or 16 kinds of $N_1N_2N_3$ represented by $N_1N_2A$ may be used, 16 kinds of $N_1N_2N_3$ represented by $N_1N_2G$ may be used, or 16 kinds of $N_1N_2N_3$ represented by $N_1N_2A$ and $N_1N_2G$ may be used.

In one translation system, 16 or more kinds of codons each represented by $N_1N_2N_3$ may be used. For example, in one translation system, 32 kinds of codons, in total, each represented by $N_1N_2N_3$, that is, 16 kinds of $N_1N_2N_3$, in total, represented by $N_1N_2U$ and $N_1N_2C$ and 16 kinds of $N_1N_2N_3$, in total, represented by $N_1N_2A$ and $N_1N_2G$ may be used.

In the present invention, an arbitrary amino acid is reassigned to $N_1N_2N_3$. In reassignment, an amino acid different from an amino acid having a codon-amino acid relation in a natural genetic code table can be assigned or an amino acid same as that in the table can be assigned. The term "natural genetic code table" as used herein means a table showing amino acids represented by genetic codes composed of an mRNA triplet, respectively, in a living body.

The present invention will hereinafter be described conveniently with a case where $N_3$ is U, that is, where $N_1N_2N_3$ is $N_1N_2U$ as an example, however, this can also be applied to a case where $N_3$ is any of A, G, and C, that is, a case where $N_1N_2N_3$ is $N_1N_2A$, $N_1N_2G$, or $N_1N_2C$, a translation system composed of $N_1N_2U$ and $N_1N_2C$, a translation system composed of $N_1N_2A$ and $N_1N_2G$, or the like.

In the natural genetic code table, $N_1N_2U$ represents the following amino acids.

TABLE 1

|  |  | $N_2$ | | | | | | | |
|---|---|---|---|---|---|---|---|---|---|
|  |  | U | | C | | A | | G | |
| $N_1$ | U | UUU | Phe | UCU | Ser | UAU | Tyr | UGU | Cys |
|  | C | CUU | Leu | CCU | Pro | CAU | His | CGU | Arg |
|  | A | AUU | Ile | ACU | Thr | AAU | Asn | AGU | Ser |
|  | G | GUU | Val | GCU | Ala | GAU | Asp | GGU | Gly |

In the present specification, therefore, for example, Phe may be assigned to UUU or an amino acid other than Phe may be assigned to it; Ser may be assigned to UCU or an amino acid other than Ser may be assigned; and any amino acid can be assigned to "$N_1N_2U$" codon. The term "assign an amino acid to a codon" means rewriting a genetic code table so that a certain codon encodes the amino acid. The term "assign an amino acid to a codon" and "reassign a codon" have the same meaning in the present specification.

Assignment, to each codon, of an amino acid different from that in the natural genetic code table is achieved by codon reassignment making use of, for example, an artificially aminoacylated RNA catalyst Flexizyme (Flexizyme). Using Flexizyme makes it possible to bind a desired amino acid to a tRNA having an arbitrary anticodon so that an arbitrary amino acid can be assigned to an arbitrary codon. Flexizyme will be described later. In the present specification, "binding an amino acid to tRNA" will be sometimes replaced by "charging tRNA with an amino acid" "aminoacylating tRNA" or "acylating tRNA with an amino acid.

In the present invention, a non-proteinogenic amino acid may be assigned to "$N_1N_2U$". A peptide library having enhanced resistance against proteolysis, cell membrane permeability, and conformational rigidity can be obtained by using as the non-proteinogenic amino acid, for example, an amino acid having a cyclic structure or an N-alkyl amino acid. Such a peptide library is useful for screening a peptide targeting an intracellular disease-associated molecule or a molecule having protease activity. When a peptide contains two or more $N_1N_2U$s, non-proteinogenic amino acids may be assigned to all of them or some of them.

In the present specification, the term "amino acid" is used in its broadest meaning and it embraces not only natural amino acids but also artificial amino acid variants and derivatives of them. The amino acids may be represented by commonly used single-letter or three-letter codes, respectively. Examples of the amino acid or derivatives thereof used herein include natural proteinogenic L-amino acids, unnatural amino acids, and chemically synthesized compounds having properties known to those skilled in the art as characteristics of an amino acid. Examples of the unnatural amino acids include, but not limited to, α,α-disubstituted amino acids (such as α-methylalanine), N-alkyl-α-amino acids, D-amino acids, β-amino acids, and α-hydroxy acids, each having a main chain structure different from that of natural amino acids; amino acids (such as norleucine and homohistidine) having a side-chain structure different from that of natural amino acids; amino acids (such as "homo" amino acids, homophenylalanine, and homohistidine) having extra methylene in the side chain thereof; and amino acids (such as cysteic acid) obtained by substituting a carboxylic acid functional group amino acid in the side chain thereof by a sulfonic acid group.

The term "amino acid" as used herein embraces proteinogenic amino acids and non-proteinogenic amino acids.

The term "proteinogenic amino acid" as used herein means an amino acid (Arg, His, Lys, Asp, Glu, Ser, Thr, Asn, Gln, Cys, Gly, Pro, Ala, Ile, Leu, Met, Phe, Trp, Tyr, or Val) constituting a protein.

The term "non-proteinogenic amino acid" as used herein means a natural or unnatural amino acid other than the proteinogenic amino acid.

A peptide library including $1 \times 10^6$ or more kinds of peptides containing an amino acid encoded by "$N_1N_2U$" is produced by the method for producing a peptide library according to the present invention.

The number of amino acids contained in each peptide and encoded by $N_1N_2U$ is not particularly limited and it can be set at, for example, 4, 5, 6, 7, 8, 9, 10, 15, 20, 30, or the like. The position of the amino acids contained in each peptide and encoded by $N_1N_2U$ is not particularly limited. The amino acids contained in each peptide and encoded by $N_1N_2U$ may be adjacent to or separated from each other.

In the method for producing a peptide library according to the present invention, an mRNA library including mRNAs which encode peptides of the peptide library, respectively, and each contain at least one $N_1N_2U$ is prepared.

The sequence of mRNAs encoding peptides of the peptide library, respectively, can be determined depending on the amino acid sequence of the peptides constituting the peptide library. Such an mRNA library can be prepared by synthesizing a DNA library encoding it and transcribing the DNA library.

In one mode of the present invention, mRNAs included in the mRNA library are each represented by the following formula (I):

$$X_1—(N_1N_2N_3)n\text{-}X_2 \qquad (I)$$

wherein, $N_1$ to $N_3$ have the meanings as described above, $X_1$ and $X_2$ each independently represent an mRNA encoding a peptide composed of an arbitrary number of amino acids, and n represents an arbitrary integer selected from 1 to 20.

A description will next be made with the case where in $N_1N_2N_3$, $N_3$ represents U, that is, $N_1N_2N_3$ is $N_1N_2U$, as an example, but the present invention can also be carried out in the case where $N_3$ is any of A, G, and C.

The term "$(N_1N_2U)n$" means that n pieces of "$N_1N_2U$" are arranged successively and it becomes a sequence encoding a variable region of peptides constituting the library, that is, a region giving diversity to peptides constituting the library. In n pieces of $N_1N_2$Us, Ns each independently represent adenine (A), guanine (G), cytosine (C) or uracil (U) so that n pieces of "$N_1N_2U$" are sometimes respectively different from one another, sometimes the same, and sometimes partially the same. Although the "n" is not particularly limited, examples of n may include 4, 5, 6, 7, 8, 9, 10, 15, and 20.

$X_1$ and $X_2$ each mean an mRNA encoding a peptide composed of an arbitrary number of amino acids. In $X_1$, the number of amino acids can be set at from 1 to 100, from 1 to 80, from 1 to 50, from 1 to 20, or the like, while in $X_2$, the number of amino acids can be set at from 0 to 100, from 0 to 80, from 0 to 50, from 0 to 20, or the like, but the number is not limited thereto. The sequence or the number of amino acids of $X_1$ and $X_2$ is determined independently and the sequence or the number of amino acids may be the same or different between them. $X_1$ has, at an N terminus thereof, an initiator amino acid charged with an initiator tRNA.

In the method for producing a peptide library according to the present invention, each mRNA of the mRNA library is then translated in a cell-free translation system to which 16 kinds of tRNAs having an anticodon to any of 16 kinds of $N_1N_2U$ codons and charged with an amino acid corresponding to the codon have been added.

The term "16 kinds of tRNAs having an anticodon to any of 16 kinds of $N_1N_2U$ codons and charged with an amino acid corresponding to the codon" as used herein means, for example, when $N_1N_2U$ represents UCU and Pro is assigned to the UCU codon, the tRNA having GGA as the anticodon and charged with Pro; and when $N_1N_2U$ represents CCU and L-pipecolic acid is assigned to the CCU codon, the tRNA having GGG as the anticodon and charged with L-pepicolic acid.

Such a tRNA can be prepared using flexizyme (Reference Documents 26, 30, and 40, Patent Documents 1 and 2). Flexizyme is an artificial aminoacylation RNA catalyst capable of acylating an arbitrary tRNA with an arbitrary amino acid or hydroxy acid. When flexizyme is used instead of aminoacyl tRNA synthesized using a natural aminoacyl tRNA synthase, a genetic code table can be rewritten by corresponding a desired amino acid or hydroxy acid to an arbitrary codon. This is called "codon reassignment".

For codon reassignment, a translation system obtained newly by removing a component from a translation system freely depending on a purpose and then reconstituting necessary components can be used. For example, when a translation system from which a specific amino acid has been removed is subjected to reconstitution, the codon corresponding to the amino acid becomes an empty codon, that is, a codon not encoding any amino acid. An arbitrary amino acid is then linked to a tRNA having an anticodon complementary to the empty codon by making use of Flexizyme or the like. After addition of the resulting tRNA, translation is performed. The arbitrary amino acid is then coded by the codon and a peptide having the arbitrary amino acid introduced therein instead of the removed amino acid is translated.

The tRNA used in the present invention may be a wild-type *Escherichia-coli* derived tRNA or an artificial tRNA prepared by in vitro transcription.

In the present invention, 16 kinds of tRNAs corresponding to 16 kinds of NNUs to be used in the translation system may have the same sequence except for an anticodon loop portion. Using such a constitution enables each tRNA to have uniform reactivity without enhancing or reducing reactivity of a specific tRNA, making it possible to express a predetermined peptide with good reproducibility.

The term "cell-free translation system" as used herein means a translation system not containing cells. As the cell-free translation system, for example, an *Escherichia coli* extract, a wheat germ extract, a rabbit reticulocyte extract, or an insect cell extract can be used. A re-constituted cell-free translation system may be used, which is obtained by reconstituting a purified ribosome protein, aminoacyl tRNA synthetase (aaRS), ribosomal RNA, amino acid, rRNA, GTP, ATP, translation initiation factor (IF), elongation factor (EF), release factor (RF), and ribosome regeneration factor, and another factor necessary for translation may be used.

The system may contain RNA polymerase for performing transcription from DNA simultaneously. Examples of the commercially available cell-free translation system usable here include *Escherichia-coli* derived systems such as "RTS-100" (trade mark) of Roche Diagnostics, reconstituted translation systems such as "PURESYSTEM" (trade mark) of PGI and "PURExpressR In Vitro Protein Synthesis Kit" of New England Biolabs, and systems using a wheat germ extract such as those of ZOEGENE Corporation or CellFree Sciences.

As a system using a ribosome of *Escherichia coli*, for example, a technology described in the following documents is known. H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

By using the cell-free translation system, a high-purity expression product can be obtained without purifying.

The cell-free translation system of the present invention may be used for not only to translation but also for transcription after addition of factors necessary for transcription.

In the method of the present invention, it is also preferred not to add a natural aminoacyl tRNA synthase corresponding to the $N_1N_2U$ codon to the cell-free translation system. In this case, the tRNA corresponding to the $N_1N_2U$ codon can be charged with an amino acid corresponding thereto by using, for example, an artificial aminoacyl tRNA synthase such as Flexizyme.

In the peptide library according to the present invention, the peptide may be macrocyclized. The term "macrocyclize" as used herein means that within one peptide, two amino acids separated from each other with a distance corresponding to one or more amino acids are bound to each other directly or indirectly via a linker or the like and thereby form a macrocyclic structure in the molecule.

The peptide can be macrocyclized via a disulfide bond, peptide bond, alkyl bond, alkenyl bond, ester bond, thioester bond, ether bond, thioether bond, phosphonate ether bond, azo bond, C—S—C bond, C—N—C bond, C=N—C bond, amide bond, lactam bridge, carbamoyl bond, urea bond, thiourea bond, amine bond, thioamide bond, or the like, but a bond is not limited to them.

The peptide may have a stable structure and have enhanced affinity for a target by macrocyclization.

For cyclization, for example, a chloroacetylated amino acid may be placed at the N terminal and Cys may be placed at the C terminal. This naturally causes cyclization of the peptide after expression by a thioether bond between the N-terminal amino acid and the C-terminal Cys. The thioether bond formed between chloroacetylated amino acid and Cys is not susceptible to degradation under reducing conditions in the living body, making it possible to increase the half-life in blood of the peptide and keep its physiologically active effect.

Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-chloromethylbenzoyl-L-phenylalanine, N-3-chloromethylbenzoyl-L-tyrosine, N-3-chloromethylbenzoyl-L-tryptophane, N-3-(2-chloroacetamido)benzoyl-L-phenylalanine, N-3-(2-chloroacetamido)benzoyl-L-tyrosine, N-3-(2-chloroacetamido)benzoyl-L-tryptophane, and D-amino acid derivatives corresponding to them.

Using, as the chloroacetylated amino acid, Nγ-(2-chloroacetyl)-α,γ-diaminobutylic acid or Nγ-(2-chloroacetyl)-α,γ-diaminopropanoic acid enables introduction in any site of the peptide chain so that a thioether bond is formed between the amino acid at any position and cysteine in the same peptide to form a cyclic structure.

The macrocyclization method can be carried out in accordance with a method described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); or Kawakami T. et al, Chemistry & Biology 15, 32-42 (2008).

The chloroacetylated amino acid and Cys may be bound to the peptide of the present invention either directly or via a linker or the like.

(Production Method of Peptide-mRNA Complex Library)

The method of producing a peptide-mRNA complex library according to the present invention is performed by, in the above-mentioned method of producing a peptide library, binding puromycin to a region downstream of ORF (open reading frame) in each mRNA when the mRNA library is prepared. Puromycin may be bound to the mRNA via a linker composed of a peptide or nucleic acid. By binding puromycin to the region downstream of ORF in the mRNA, a ribosome which has translated the ORF in the mRNA incorporates therein puromycin to form an mRNA-peptide complex. Such a peptide-mRNA complex can be used in in vitro display, because it allows genotype-phenotype linkage.

(Library)

The present invention embraces a peptide library and a peptide-mRNA complex library produced by the above-mentioned production method.

In one mode, the peptide library according to the present invention is encoded by an mRNA library represented by the following formula (I):

$$X_1—(N_1N_2N_3)n\text{-}X_2 \qquad (I)$$

[wherein, $N_1$, $N_2$, and $N_3$ are each independently selected from adenine (A), guanine (G), cytosine (C), and uracil (U); an arbitrary amino acid is reassigned to each $N_1N_2N_3$; $X_1$ and $X_2$ each independently represent an mRNA encoding a peptide composed of an arbitrary number of amino acids; and n represents an arbitrary integer selected from 4 to 20].

Details of $X_1$, $X_2$, $N_1$, $N_2$, $N_3$, and n are as described above. For example, the mRNA library may contain only an initiator amino acid as $X_1$ while having no $X_2$.

In one mode of the peptide-mRNA complex library according to the present invention, in the peptide library encoded by the mRNA library represented by the above formula (I), the peptides form complexes with mRNAs encoding the peptides themselves, respectively.

The library according to the present invention is useful for screening of a peptide binding to a target molecule. In particular, using, as an amino acid encoded by an NNU codon, a non-proteinogenic amino acid capable of enhancing resistance against proteolysis, cell membrane permeability, and conformational rigidity is also useful for screening of a drug candidate targeting a molecule such as intracellular molecule or molecule having protease activity, which cannot be targeted when the conventional peptide library is used.

In the peptide library or peptide-mRNA complex library according to the present invention, the peptide may be macrocyclized and such a structure is also embraced in the present invention.

(Screening Method)

The present invention also provides a screening method for identifying a peptide that binds to a target substance by using the peptide library produced by the method of the present invention.

In one mode, the screening method of the present invention includes a step of bringing the peptide library produced by the method of the present invention into contact with a target substance, followed by incubation.

The target substance is not particularly limited in the present specification and examples include low molecular compounds, high molecular compounds, nucleic acids, peptides, proteins, sugars, and lipids. In particular, the library of the present invention can be used also when the target substance has protease activity or it is an intracellular molecule.

The target substance immobilized onto, for example, a solid-phase support may be brought into contact with the library of the present invention. The term "solid-phase support" as used herein is not particularly limited insofar as it can immobilize the target substance thereonto. Examples include microtiter plates, substrates, and beads made of glass, a metal, a resin, or the like, nitrocellulose membranes, nylon membranes, and PVDF membranes. The target substance can be immobilized onto such a solid phase support in a known manner.

The target substance and the library are brought into contact with each other in a buffer selected as needed and they are interacted while controlling pH, temperature, time, and the like.

In one mode, the screening method of the present invention further includes a step of selecting a peptide that has bound to the target substance. The peptide that has bound to the target substance is selected, for example, by labeling peptides with a detectable label by a known method and after the step of bringing the library into contact with the target substance, washing the surface of the solid phase support with a buffer, and then detecting the compound that has bound to the target substance.

Examples of the detectable label include enzymes such as peroxidase and alkaline phosphatase, radioactive substances such as $^{25}I$, $^{131}I$, $^{35}S$, and $^{3}H$, fluorescent substances such as fluorescein isothiocyanate, rhodamine, dansyl chloride, phycoerythrin, tetramethyl rhodamine isothiocyanate, and near infrared fluorescent materials, light-emitting substances such as luciferase, luciferin, and aequorin, and nanoparticles such as gold colloid and quantum dot. When an enzyme is used as the label, the compound can be detected by adding a substrate of the enzyme to develop a color. The compound can also be detected by binding biotin to the peptide and then binding avidin or streptavidin labeled with an enzyme or the like to the biotin-bound peptide.

The screening method can not only detect or analyze the presence/absence or degree of binding but also analyze the enhanced or inhibited activity of the target substance and thereby identify a peptide having such enhanced or inhibited activity. Such a method also allows identification of a peptide having physiological activity and useful as a drug.

In the case of the peptide-mRNA library, screening can be carried out using the TRP display method (Reference Documents 48 and 49).

In this case, after reverse transcription reaction of the peptide-mRNA complex library, the library is brought into contact with a target substance. A complex that binds to the target substance is selected and its DNA is amplified by PCR. By adding this DNA to a TRAP reaction system, a peptide-mRNA complex library is constructed again. Similar operations are repeated.

Since as a result of the repetition, a peptide-RNA complex having high affinity for the target substance is obtained in concentrated form, a peptide that binds to the target substance can be identified efficiently by analyzing the sequence of the DNA of the concentrated complex.

(Screening Kit)

The present invention also provides a kit for screening a peptide.

In one mode, the screening kit of the present invention includes the peptide library or the peptide-mRNA complex library produced by the production method of the present invention.

The screening kit of the present invention includes, in addition, a reagent and an apparatus necessary for detecting the binding between a target substance and a peptide or peptide-mRNA complex. Examples of such a reagent and apparatus include, but not limited to, solid phase supports, buffers, labeling reagents, enzymes, enzyme reaction terminator solutions, and microplate readers.

(Translation System)

The present invention embraces a translation system including only the following (a) and (b) as tRNA:

(a) initiator tRNAs, and (b) elongator tRNAs having base sequences 85% or more identical to one another in whole length.

As described above, the present inventors have developed a translation system in which $N_1N_2N_3$ encodes an arbitrary amino acid, by codon reassignment making use of Flexizyme. In a natural translation system, tRNAs having an anticodon to each amino acid are present and each tRNA has a specific sequence also in a region other than an anticodon loop.

When an arbitrary amino acid is reassigned to each $N_1N_2N_3$ by making use of Flexizyme, all the tRNAs may be artificial. In this case, respective elongator tRNAs corresponding to $N_1N_2N_3$s to be added to the translation system may have base sequences 80% or more, 85% or more, 88% or more, or 90% or more identical to one another in total length. This means that an elongator tRNA group almost equal in the sequence except for anticodon can be used. In the elongator tRNA group, they may have base sequences identical to one another except for an anticodon loop. In the respective elongator tRNAs corresponding to $N_1N_2N_3$s to be added to the translation system, sequences except for an anticodon loop may be 85% or more, 88% or more, 90% or more, 93% or more, 95% or more, 98% or more, or 99% or more identical to one another.

The term "anticodon loop" as used herein means a loop portion of a single strand of a tRNA containing an anticodon. The sequence of the anticodon loop can be determined as needed by those skilled in the art so as to complement the codon-anticodon interaction (Reference Document 45).

The translation system thus obtained includes only one kind of initiator tRNAs and one kind of elongator tRNAs (tRNAs having almost the same base sequence except for anticodon) so that the reactivity of the tRNAs is uniform and predetermined peptides can therefore be obtained with good reproducibility.

According to the translation system of the present invention, a library including $1 \times 10^6$ or more respectively different peptides can be produced based on the diversity of $N_1N_2N_3$ in the mRNA.

The translation system of the present invention may be used for transcription after adding a factor necessary for transcription. The translation system of the present invention is suited for use in the method for producing a peptide library according to the present invention.

The complete disclosure of the patent documents and reference documents cited herein are incorporated herein by reference.

Examples

The present invention will hereinafter be described specifically based on Examples, but the present invention is not limited to or by them. Those skilled in the art can change the present invention into various modes without departing from the gist of the present invention and such a change is also embraced within the scope of the present invention.

In the present example, by comprehensively screening various CNAs with respect to incorporation in a peptide in the presence of a ribosome catalyst by using Flexizyme (Reference Documents 26, 39, and 40), various CNAs efficiently and suitably incorporated in a peptide backbone were identified. In addition, possibility of template DNA-dependent expression of highly N-alkylated polycyclic peptidomimetics was searched by assigning respectively different 16 CNAs to 16 NNU codons by codon reassignment. Lastly, in order to study the conformity between the library of the completely N-alkylated polycyclic peptidomimetics and the in vitro TRAP (transcription/translation coupled with association of puromycin-linker) display method (FIG. 1B) recently developed by the present inventors, an efficiency of displaying the random library of completely N-alkylated polycyclic peptidomimetics on the mRNA encoding them was measured.

A translation system was prepared in which 16 NNU codons were assigned to proteinogenic amino acids and non-proteinogenic amino acids other than CNA was prepared by adding an aminoacyl tRNA synthesized using Flexizyme without adding any of aminoacyl synthase and wild-type tRNA. As a result of ribosome synthesis of a peptide using the present translation system, a peptide having a desired amino acid incorporated therein was detected. Details will next be described.

[Method]

1. Preparation of tRNA and Flexizyme Used for Translation tRNAs to be aminoacylated by Flexizyme were prepared by in vitro transcription according to JPA 2008-125396. Following chemically synthesized oligonucleotides to be used as a raw material were purchased from Operon Biotechnologies.

P1:
(SEQ ID NO: 1)
5'-GAACCAGTGACATACGGATTTTCAGTCCGCCGTTCTACCGACT-3'

P2:
(SEQ ID NO: 2)
5'-GAACCAGTGACATACGGAACCTCAATCCGCCGTTCTACCGACT-3'

P3:
(SEQ ID NO: 3)
5'-GAACCAGTGACATACGGATTATCAGTCCGCCGTTCTACCGACT-3'

P4:
(SEQ ID NO: 4)
5-GAACCAGTGACATACGGAATGTCAATCCGCCGTTCTACCGACT-3'

P5:
(SEQ ID NO: 5)
5'-GAACCAGTGACATACGGATTTCCAGTCCGCCGTTCTACCGACT-3'

P6:
(SEQ ID NO: 6)
5'-GAACCAGTGACATACGGAACCCCATTCCGCCGTTCTACCGACT-3'

P7:
(SEQ ID NO: 7)
5'-GAACCAGTGACATACGGATTACCAATCCGCCGTTCTACCGACT-3'

P8:
(SEQ ID NO: 8)
5'-GAACCAGTGACATACGGACTGCCAGTCCGCCGTTCTACCGACT-3'

P9:
(SEQ ID NO: 9)
5'-GAACCAGTGACATACGGATTTACAGTCCGCCGTTCTACCGACT-3'

P10:
(SEQ ID NO: 10)
5'-GAACCAGTGACATACGGATTCACAATCCGCCGTTCTACCGACT-3'

P11:
(SEQ ID NO: 11)
5'-GAACCAGTGACATACGGATTAAGAGTCCGCCGTTCTACCGACT-3'

P12:
(SEQ ID NO: 12)
5'-GAACCAGTGACATACGGATTGACAATCCGCCGTTCTACCGACT-3'

P13:
(SEQ ID NO: 13)
5'-GAACCAGTGACATACGGATTTGCAGTCCGCCGTTCTACCGACT-3'

P14:
(SEQ ID NO: 14)
5'-GAACCAGTGACATACGGATCCGCAGTCCGCCGTTCTACCGACT-3'

P15:
(SEQ ID NO: 15)
5'-GAACCAGTGACATACGGATTAGCAGTCCGCCGTTCTACCGACT-3'

P16:
(SEQ ID NO: 16)
5-GAACCAGTGACATACGGATTGGCAATCCGCCGTTCTACCGACT-3'

P17:
(SEQ ID NO: 17)
5-GAACCAGTGACATACGGATTATGAGTCCGCCGTTCTACCGACT-3'

P18:
(SEQ ID NO: 18)
5'-GTAATACGACTCACTATAGGCTCTGTAGTTCAGTCGGTAGAACGGCGGA-3'

P19:
(SEQ ID NO: 19)
5'-TGGCGGCTCTGACTGGACTCGAACCAGTGACATACGGA-3'

P20:
(SEQ ID NO: 20)
5'-GGCGTAATACGACTCACTATAG-3'

P21:
(SEQ ID NO: 21)
5'-TGGCGGCTCTGACTGGACTC-3'

A portion of the tRNA, that is, a transcription product, becoming an anticodon loop was underlined in SEQ ID NO: 1 to 17. For example, the underlined portion TTTTCAG of SEQ ID NO: 1 is CUGAAAA in tRNA and GAA at the center thereof corresponds to an anticodon and corresponds to a codon UUC or UUU on the mRNA.

A tRNA was obtained by performing an overlap extension reaction using SEQ ID NO: 18 and each of SEQ ID NOS: 1 to 17, performing a first PCR reaction using SEQ ID NO: 19 and SEQ ID NO: 20 as a primer, performing a second PCR reaction using SEQ ID NO: 20 and SEQ ID NO: 21 as a primer, and transcribing the resulting DNA. The tRNA thus obtained has the following sequence:

(SEQ ID NO: 84)
GGCUCUGUAGUUCAGUCGGUAGAACGGCGGANNNNNNNUCCGUAUGUC
ACUGGUUCGAGUCCAGUCAGAGCCGCCA (wherein,
NNNNNNN represents an anticodon loop).

A translation initiator tRNA, Flexizyme eFx, and Flexizyme dFx were prepared using the material and method described in JPA 2008-125396.

2. Ribosome Synthesis of a Peptide Containing One Cyclic N-Alkyl Amino Acid

A translation reaction liquid containing 0.04 µM of template DNA, 0.5 mM of each of Met, Tyr, and Lys, 50 µM of [$^{14}$C]-Asp, 0.03 µM of MetRS, 0.02 µM of TyrRS, 0.11 µM of LysRS, 0.13 µM of AspRS, and 200, 100, 50, 25, or 12.5 µM of cyclic N-alkylaminoacyl-tRNA$^{Asn-E2}$ (GGA) was incubated at 37° C. for 60 minutes. The reaction product was analyzed by tricine-SDS PAGE and autoradiography (Pharox FX, BIO-RAD). For MALDI-TOF-MS analysis, Asp was used instead of [$^{14}$C]-Asp; 100 µM of cyclic N-alkylaminoacyl-tRNA$^{Asn-E2}$ (GGA) was added to cause a reaction. After the translation product was desalted with C-TIP (Nikkyo Technos) and eluted with 80% acetonitrile and 0.5% acetic acid saturated with CHCA, analysis was made in a linear positive mode of Autoflex II (BRUKER DALTON ICS).

3. Ribosome Synthesis of Bis-N-Alkyl Bicyclic Peptide, Tris-N-Alkyl Tricyclic Peptide, and Tetra-N-Alkyl Tetracyclic Peptide A translation reaction liquid containing 0.04 µM of template DNA, 0.5 mM of each of Met, Tyr, and Arg, 0.03 µM of MetRS, 0.02 µM of TyrRS, 0.03 µM of ArgRS, 50 µM of each of cyclic N-alkylaminoacyl-tRNA$^{Asn-E2}$s, and 5 µM of in vitro transcribed tRNA$^{fMet}$ (CAU) was incubated at 37° C. for 60 minutes. MALDI-TOF-MS analysis was performed as described above.

4. Measurement of Display Efficiency of Proteinogenic Peptide and N-Alkyl Polycyclic Peptide In a TRAP system not containing an extracted natural tRNA but containing 0.5 mM of each of Ser and Trp, 0.04 µM of SerRS, 0.03 µM of TrpRS, 2.5 µM of a mRNA library, 10 µM of EF-P, 2.5 µM of a puromycin-DNA linker, 20 µM of biotinyl-Phe-tRNA$^{fMet}$ (CAU), 10 µM of each of 16 cyclic N-alkylaminoacyl tRNA$^{Asn-E2}$ s, and 5 µM of each of tRNAse$^{Ser}$ (CAU) and tRNA$^{Trp}$ (CCA), a random (NNU)$_8$ mRNA library was incubated at 37° C. for 25 minutes to translate it into a biotinylated N-alkyl polycyclic peptide library. After the reaction, cDNA was synthesized by reverse transcription. The peptide-displayed mRNA was then selectively collected using streptavidin-immobilized magnetic beads.

For a proteinogenic peptide library, a TRAP system not containing Met, Gln, Lys, and Glu as an amino acid, but containing 20 kinds of aaRSs, 2.5 µM of an mRNA library, 2.5 µM of a puromycin-DN-linker, 20 µM of biotinyl-Phe-tRNA$^{fMet}$ (CAU), an extracted natural tRNA mixture, and 5 µM of in vitro transcribed tRNA$^{Ser}$ (CAU) was used. The reverse transcription reaction and streptavidin pull down were performed as described above.

5. Translational Synthesis without Aminoacyl tRNA Synthase and Wild-Type tRNA

Amino acids were all converted into a 3,5-dinitrobenzyl ester or cyanomethyl ester by the method described in Reference Documents 26, 12, and 13, and JPA 2008-125396 and used as a substrate of Flexizyme. Thirteen amino acids were prepared as a 3,5-dinitrobenzyl ester and they were π-methyl-histidine (His(3-Me)), L-arginine (Arg), L-alanine (Ala), N-methyl-L-alanine ($^{Me}$Ala), glycine (Gly), N-methyl-glycine ($^{Me}$Gly), L-histidine (His), L-isoleucine (Ile), N-methyl-L-norleucine ($^{Me}$Nle), L-lysine (Lys), cyclo-leucine (Cle), N-n-butyl-glycine ($^{Bu}$Gly), and L-cysteine (Cys). Five amino acids were converted into a cyanomethyl ester and they were L-tyrosine (Tyr), N-methyl-L-phenyl-alanine ($^{Me}$Phe), N-(2-phenylethyl)-glycine (PheEtGly), L-tryptophan (Trp), and N-chloroacetyl-L-pheylalanine ($^{ClAc}$Phe). In accordance with the combination listed in the genetic code table shown in Table 2, the 3,5-dinitrobenzyl ester and the cyanomethyl ester were reacted with a tRNA in the presence of Flexizyme dFx and Flexizyme eFx, respectively. The aminoacyl tRNA was purified by the precipitation operation as described in JPA 2008-125396 and was then dissolved before translation.

TABLE 2

| 1$^{st}$ Letter | 2$^{nd}$ Letter | | | |
|---|---|---|---|---|
| | U | C | A | G |
| U | His(3-Me) | Gly | Ile | Cle |
| C | Arg | $^{Me}$Gly | $^{Me}$Nle | $^{Bu}$Gly |
| A | Ala | His | Lys | $^{PheEt}$Gly |
| G | $^{Me}$Ala | Tyr | $^{Me}$Phe | Trp |

3$^{rd}$ Letter: U or C
Initiation (AUG): $^{ClAc}$Phe, AUG (elongation): Cys

A solution obtained by dissolving the aminoacyl tRNA in a sodium acetate buffer (pH 5.2) was added to an *Escherichia coli*-derived reconstituted translation system prepared without adding a free amino acid, an *Escherichia coli*-derived wild-type tRNA, and an aminoacyl tRNA synthase. It was added so that the tRNA reacted with an N-chloroacetyl-L-phenylalanine or L-cysteine ester had a final concentration of 50 µM and 16 kinds of tRNAs corresponding to the NNU codon aminoacylated with the other amino acid ester had a final concentration of 25 µM. A template DNA having an ORF as described in FIG. 8 was added at a concentration of about 100 nM. After the resulting mixture was allowed to stand at 37° C. for 20 minutes, the peptide was desalted and purified with a reverse phase chip and detected using MALDI-TOF-MS.

[Results]

1. Screening of Cyclic N-Alkyl Amino Acid (CNA) Used for Codon Rearrangement

Twenty one purchasable CNAs including 13 CNAs which had not been used so far for research were used (FIG. 1A). All the twenty one CNAs were chemically induced into a 3,5-dinitroenzyl ester or cyanomethyl ester and converted into a substrate of Flexizyme corresponding thereto. The tRNA acylation conditions of the CNAs with Flexizyme were optimized using an activated ester derivative and a microhelix RNA, which was an analog of tRNA prepared by in vitro translation. As a result of quantitative determination of a production efficiency of a CNA-microhelix RNA by isolating it with Acid urea PAGE, it was confirmed that all the CNAs were charged onto the microhelix RNA and the yield exceeded 25% under the optimal conditions (FIG. 1C). The resulting yield was presumed to be sufficient for translation assay based on the past researches (Reference Documents 12 and 13) on the translation substrate screening using Flexizyme.

The Asn tRNA (tRNA$^{Asn-E2}$) (Reference Document 30) of a modified *Escherichia coli* having an anticodon GGA was aminoacylated with CNA in the presence of Flexizyme under optimum conditions. By using the CNA-tRNA$^{Asn-E2}$ (GGA) thus obtained and DNA encoding fMet-(Lys)$_3$-CNA-FLAG (SEQ ID NO: 22) peptide, an incorporation assay in one place at UCC codon was performed (FIG. 2A). Peptide synthesis was performed using a transcription/translation coupling system containing only four kinds (Met, Lys, Asp and Tyr) of proteinogenic amino acids and their cognate aaRSs. For comparison, the same DNA was transcribed into fMet-(Lys)$_3$-Pro-FLAG and then translated using Pro-tRNA$^{Asn-E2}$ (GGA) prepared using a proline-3,5-dinitrobenzyl ester and Flexizyme. The yield of the peptide was calculated based on incorporation of [$^{14}$C]-Asp Asp (in the sequence downstream of the CNA residue) into the fMet-(Lys)$_3$-CNA-FLAG peptide. Sixty minutes later, SDS was added to terminate the translation reaction and the peptide product was detected by autoradiography after Tricine SDS-PAGE.

Figure 2C:
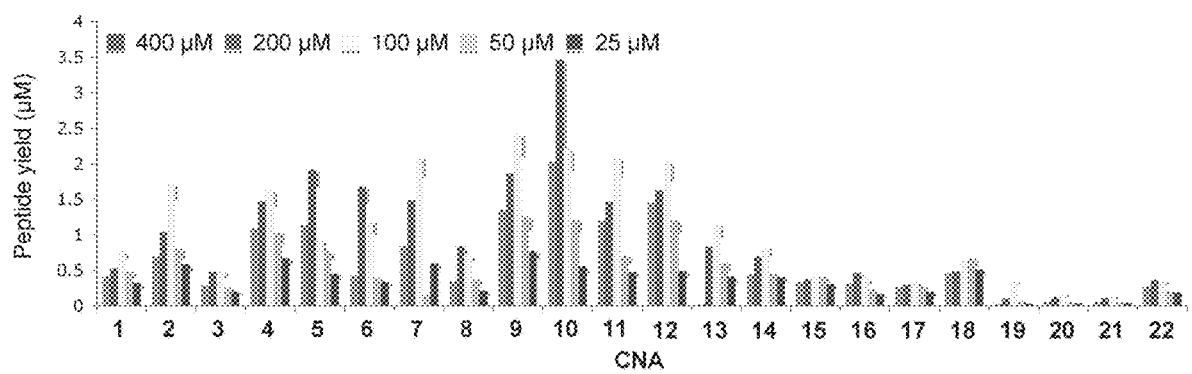
FIG. 2C shows the concentration of Peptide 1 expressed in the presence of 400 μM, 200 μM, 100 μM, 50 μM, or 25 μM of CNA-tRNA.

FIG. 2B shows that almost half of the CNAs is incorporated in the peptide more efficiently than proteinogenic proline. The incorporation efficiency of the remaining CNAs was lower than that of the proteinogenic proline, but in the presence of 100 µM of the corresponding CNA-tRNA, the concentration of the peptide in which the CNA was incorporated exceeded 0.1 µM (FIG. 2C).

Figure 2D:
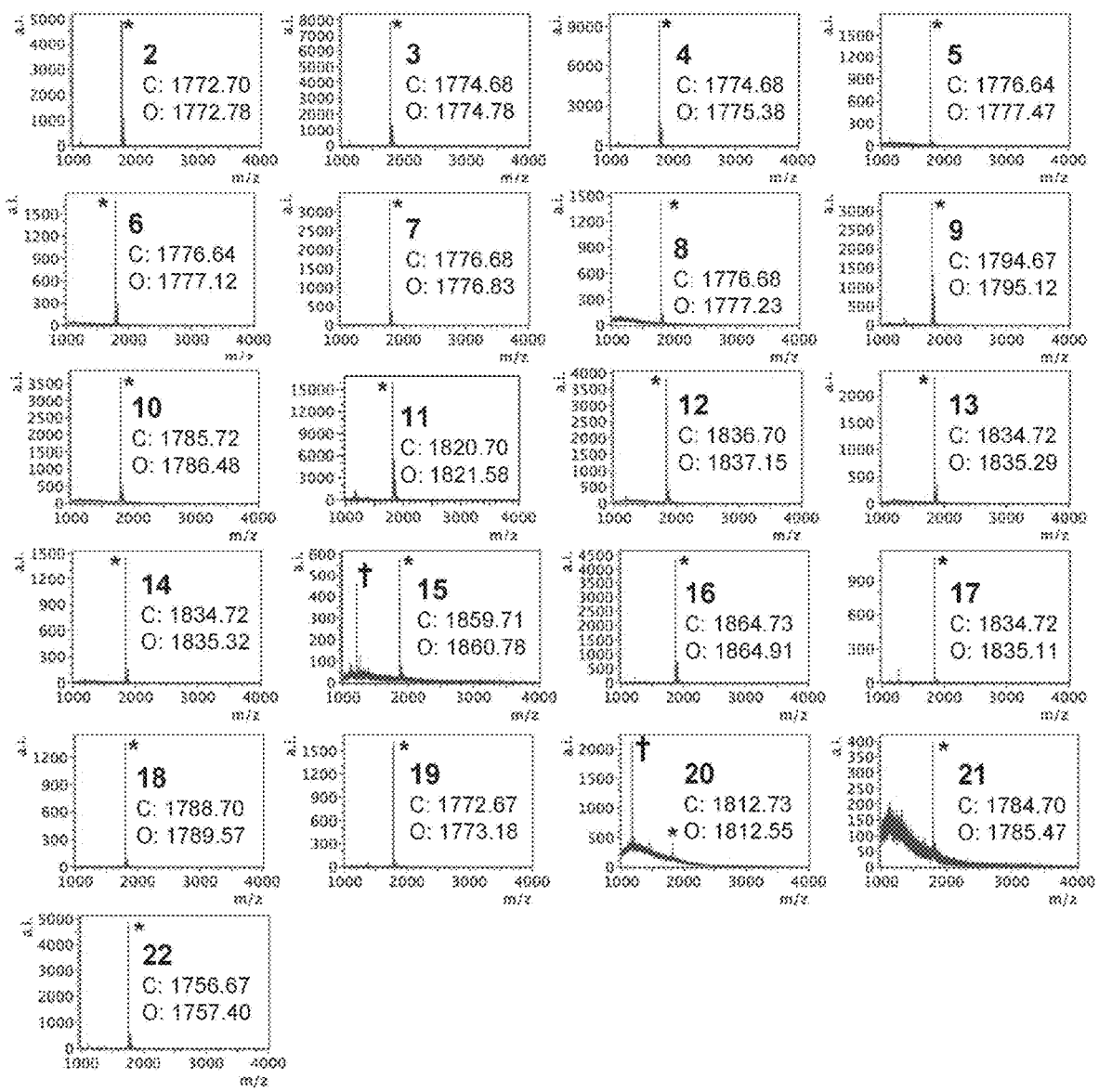
FIG. 2D shows, on the upper side thereof, mRNA2 used for incorporation assay of CNA in one site and Peptide 2 encoded by mRNA2. CNA was assigned to the empty codon UCC.

Then, in the presence of 100 µM of CNA-tRNA, a translation product synthesized from DNA encoding fMet-(Tyr)$_3$-CNA-FLAG (SEQ ID NO: 23) was desalted and subjected to MALDI-TOF analysis. As a result, it was confirmed that all the CNAs were incorporated in the peptide (FIG. 2D). From CNAs 15 and 21, however, a short peptide was detected as a byproduct generated by elongation behind the CNA incorporation site. This is presumed to occur due to slow formation of an N-alkyl peptide bond between a new peptide and these CNAs.

Figure 2E:
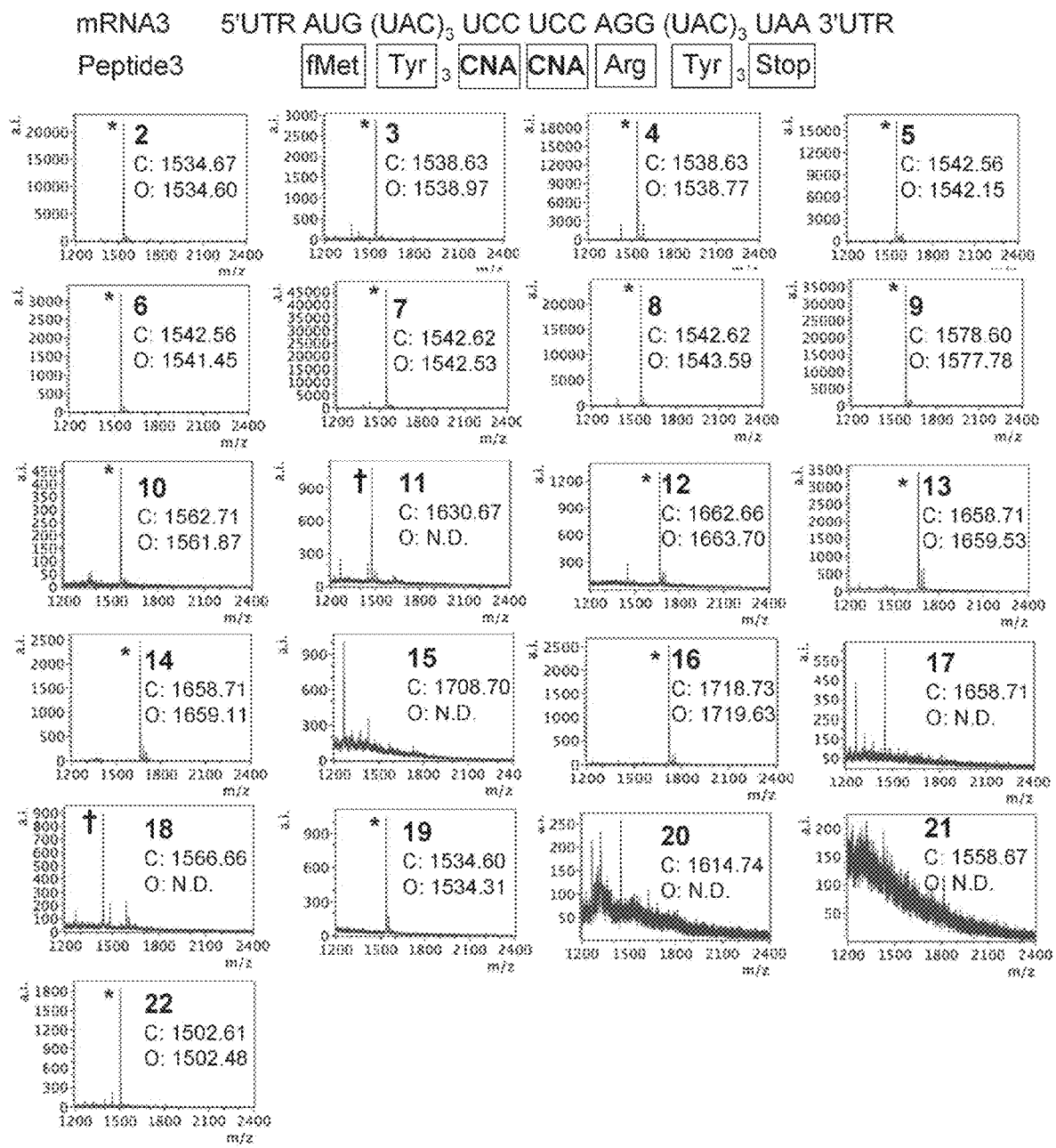
FIG. 2E shows, on the upper side thereof, mRNA3 used for incorporation assay of CNA in two successive sites and Peptide 3 encoded by mRNA3. CNA was assigned to the empty codon UCC.

To study the incorporation of a CNA further, a DNA encoding a fMet-(Tyr)$_3$-(CNA)$_2$-Arg-(Tyr)$_3$ (SEQ ID NO: 24) peptide was prepared and successive incorporation of two CNAs in two successive UCC codon positions was confirmed (FIG. 2E). A translation system for peptide expression was constructed from three proteinogenic amino acids (Met, Tyr, and Arg) and cognate aaRSs thereof. MALDI-TOF-MS analysis of the desalted translation product has revealed that 15 CNAs (2-10, 12-14, 16, 19, and 22 in FIG. 1A) were incorporated into the peptide successfully (FIG. 2E). These 15 CNAs and proline were therefore used in an experiment performed later.

Figures 3A, 3B, 3C:
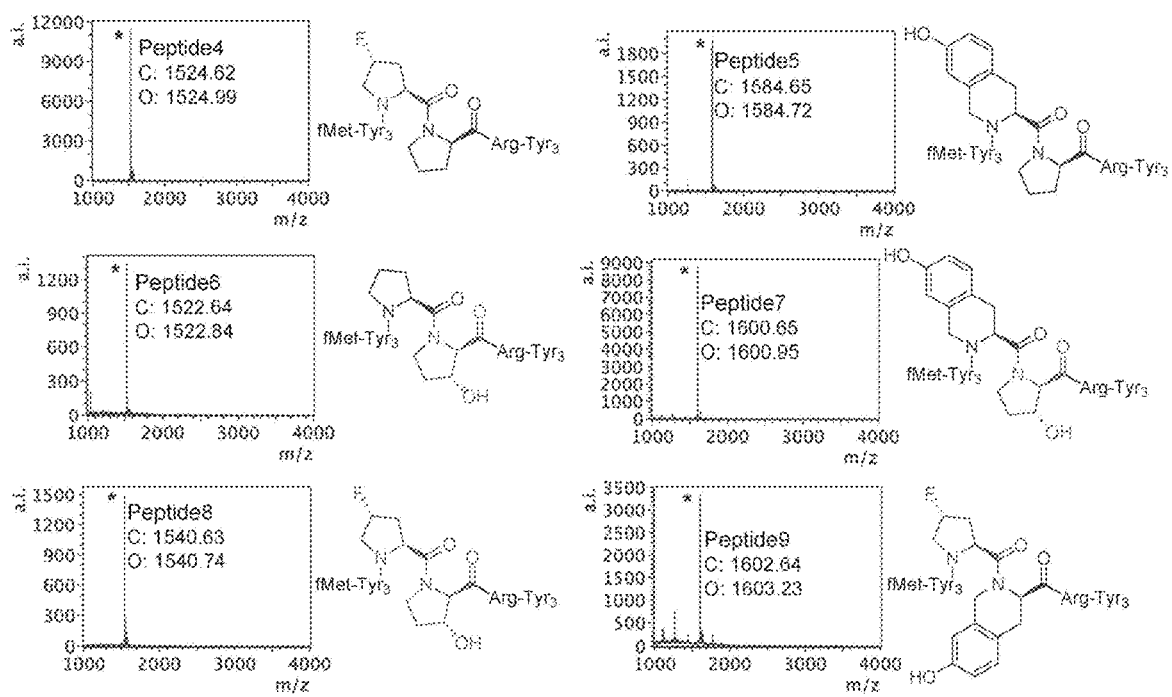
FIG. 3A shows the sequences of template mRNAs 4 to 9 and bis-N-alkyl bicyclic peptides 4 to 9 encoded thereby, respectively.
FIG. 3B shows a genetic code for synthesis of bis-N-alkyl bicyclic peptides by DNA programming. Four NNU codons were assigned to four different CNAs.
FIG. 3C shows MALDI-TOF-MS spectra and the structure of bis-N-alkyl bicyclic peptides. Calculated molecular mass (C) and observed molecular mass (O) of a monovalent ion [M+H]⁺ are shown in each spectrum. An asterisk (*) represents a peak corresponding to each of the bis-N-alkyl bicyclic peptides.

2. Codon Reassignment in Synthesis of Highly N-Alkylated Polycyclic Peptidomimetics Feasibility of codon reassignment, more specifically, assignment of 16 NNU codons to respectively different 16 CNAs was studied. The most concerning factor in achieving correct decoding of 16 NNU codons into corresponding CNAs was misreading, in the first or second codon base of the NNU codon, of an A-U pair or G-C pair for a G-U pair (FIG. 3D) (Reference Documents 41 to 47). As shown in FIG. 3A, therefore, mRNAs containing two respectively different codons selected from four codons (UUU, UCU, CUU, and CCU) were designed and DNA templates corresponding thereto were prepared. These four test codons were near-cognate from one another and there was a possibility that three of them were misread for a G-U base pair by near-cognate aa-tRNAs corresponding thereto (FIG. 3D). Four kinds of tRNAs having tRNA$^{Asn-E2}$ as a main body and different in anticodon loop were prepared. According to the reprogrammed genetic code shown in FIG. 3B, CNAs (12, 1, 8, and 3) were charged onto the tRNAs, respectively.

A translation system was constructed using, instead of a native base-modified tRNA mixture, in vitro transcribed tRNA$^{fMet}$ (CAU), tRNA$^{Tyr}$ (CUA), and tRNA$^{Arg}$ (CCG) so that all the 16 NNU codons became empty codons. The tRNA$^{Tyr}$ (CUA) was tyrosylated with TyRS to read a UAG codon (FIG. 3B). The transcription/translation products obtained using 6 DNA templates were desalted and subjected to MALDI-TOF-MS analysis. As a result, it was confirmed that six programmed bis-N-alkyl bicyclic peptides were synthesized as a main product (FIG. 3C).

In addition, it was studied whether translation of mRNA containing three respectively different codons selected from four kinds of codons (UUU, UCU, CUU, and CCU) used in the bis-N-alkyl bicyclic peptide synthesis enabled successive incorporation of three respectively different CNAs (FIG. 4A).

The translation products were desalted and subjected to MALDI-TOF-MS analysis. It was found that as expected, a tris-N-alkyl tricyclic peptide was formed as a main product from any of four templates in the translation reaction using template DNAs (FIG. 4B). It was confirmed based on the above experiment that in DNA-programmed synthesis of a desired bis-N-alkyl bicyclic peptide and tris-N-alkyl tricyclic peptide, four near-cognate codons (UUU, UCU, CUU, and CCU) were decoded correctly and the intended CNAs can be incorporated without misreading.

Since in the DNA-programmed N-alkyl polycyclic peptidomimetics, the four near-cognate codons were decoded correctly, codon reassignment for assigning respectively different CNAs to 16 NNU codons was tried.

A template mRNA14 including the four different NNU codons (UUU, UCU, CUU, and CCU) used in the above experiment was designed (FIGS. 5A and 5B). It was added to a translation system having a genetic code (FIG. 5B) based on which codon reassignment was performed. The codon arrangement was performed by adding, to the translation system, tRNA$^{Asn-E2}$s respectively charged with CNAs (12, 1, 8, and 3 of FIG. 1A) and different only in the sequence of an anticodon loop. MALDI-TOF-MS analysis showed that a desired tetra-N-alkyl tetracyclic peptide 14 was synthesized correctly from the template mRNA14 (FIG. 5C).

Three template mRNAs 15, 16, and 17 containing 12 NNU codons (FIGS. 5A and 3D) were designed. They were added to a translation system having the genetic code (FIG. 5B) based on which codon reassignment was performed. Incidentally, codon reassignment was performed, similar to the above-described one, by adding to the translation system, 12 tRNAs having tRNA$^{Asn-E2}$ as a main body and different only in the sequence of an anticodon loop. MALDI-TOF-MS analysis showed that desired tetra-N-alkyl tetracyclic peptides 15 to 17 were synthesized correctly from the template mRNAs 15 to 17, respectively (FIG. 5C).

The above experiment showed that in the DNA-programmed synthesis of a tetra-N-alkyl tetracyclic peptide, 16 NNU codons were assigned correctly to 16 different CNAs and misreading due to near cognate did not occur (FIGS. 5B and 3D).

3. TRAP Display of Completely N-Alkylated Polycyclic Peptidomimetics Random Library Since codon reassignment technology for assigning 16 NNU codons to 16 respectively different CNAs was developed, a display efficiency of completely N-alkylated polycyclic peptidomimetics library based on random NNU mRNA library was evaluated by the TRP display developed recently by the present inventors.

The TRP display uses a transcription/translation coupled system containing puromycin bound to the 3' end of an oligo DNA linker complementary to the 3' end of mRNA. In the TRAP system, DNA is transcribed and translated in a reaction system to form a peptide and the peptide thus expressed is automatically displayed (trapped) on the mRNA encoding the peptide itself via a puromycin DNA linker.

Prior to evaluation of a display efficiency of the completely N-alkylated polycyclic peptidomimetics library, some spacer sequences not containing an NNU codon were evaluated (FIGS. 6A and 6B). A spacer sequence having a high display efficiency was identified by reassigning a biotin-modified amino acid to a C-terminal constant region, performing streptavidin pull-down, and measuring a display efficiency. It has been revealed that the $(AUG)_4$ spacer had the highest peptide display efficiency (FIG. 6B).

Similar pull-down analysis has revealed that an increase in distance between the first empty UAG codon on the mRNA and a puromycin DNA linker annealing region decreased the peptide display efficiency (FIG. 6C). This has suggested low possibility of puromycin attacking an immature peptide during translation upstream of the spacer region of the mRNA.

On the other hand, when CNAs (15 and 21) having a low introduction efficiency were used, expression of a C-terminal cleavage peptide was observed (FIG. 2D). This suggested the possibility of a peptide display efficiency being not evaluated accurately because the C-terminal cleavage peptide was displayed in the above-described method of reassigning the biotin-modified amino acid to the C-terminal constant region. In order to evaluate the display efficiency accurately, a translation system in which a biotin-modified amino acid was reassigned to the N terminal was used in the following experiment.

Figures 7B, 7C, 7D:
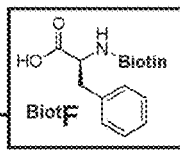
FIG. 7B shows the respective sequences of the mRNA library and the peptide library used for measurement of display efficiency. The initiator AUG codon was assigned to $^{Biot}$F. An empty UAG codon tethering ribosome for increasing a transfer efficiency of the peptide to puromycin is underlined. The puromycin-DNA linker annealing region is shown in italics. Xaa represents a random CNA or proteinogenic amino acid.
FIG. 7C shows a genetic code for the expression of a library of proteinogenic peptides and complete N-alkyl polycyclic peptidomimetics.
FIG. 7D shows a display efficiency of proteinogenic peptides and complete N-alkyl polycyclic peptidomimetics.

The display efficiency of the completely N-alkylated polycyclic peptidomimetics was evaluated by constructing an NNU mRNA library encoding a peptide library including eight random CNA residues and an $(AUG)_4$ spacer (FIG. 7B). N-biotinylated Phe-tRNA was used for labeling the N terminal of the peptide with biotin (FIG. 7A). To the TRAP system, Met was not added in order to assign an initiator AUG codon to $^{Bio}F$ but tRNA$^{Ser}$ (CAU) charged with Ser by means of in vitro transcribed SerRS was added in order to assign the spacer AUG codon to Ser (FIGS. 7B and C). Since the template mRNA was already found to have a peptide display efficiency higher than that of the template DNA, the template mRNA was added to the TRAP system instead of the template DNA.

The display efficiency of the biotinylated completely N-alkylated polycyclic peptidomimetics on the respective mRNAs thereof by streptavidin pull-down of a translation product containing 16 kinds of pre-charged CNA-tRNA$^{Asn-E2}$ (on the right side of FIG. 7C) was found to be 1.9% (FIG. 7D). On the other hand, as a result of similar streptavidin pull-down assay of the translation product of control (on the left side of FIG. 7C), the display efficiency of a biotinylated proteinogenic peptide on the mRNA encoding it was 10.7% (FIG. 7D). It has been understood from the above results that the display efficiency of N-alkyl polycyclic peptidomimetics was about ⅕ of that of a peptide composed of a proteinogenic amino acid corresponding thereto. This suggests that in a 0.5 mL translation reaction liquid, about $10^{13}$ unique completely N-alkylated polycyclic peptidomimetics can be displayed on the mRNAs encoding them.

4. Translational Synthesis Using Only Aminoacyl tRNA Synthesized Outside the Translation Reaction System As has already been proved in the above experiment, using Flexizyme enables NNU codons and CNA amino acids to correspond to each other without being limited by their kinds. It was therefore verified next that the method for producing a library according to the present invention could be performed without depending on the correspondence between an amino acid and a codon defined by an aminoacyl tRNA synthase or wild-type tRNA. In this experiment, a translation system was prepared by aminoacylating all the tRNAs corresponding to an AUG codon and 16 NNU codons by using Flexizyme, adding them together with a similarly aminoacylated initiator tRNA to a cell-free translation system, while not adding thereto any of an aminoacyl tRNA synthase, a wild-type tRNA, and a free amino acid. In the resulting translation system, a thioether cyclic peptide composed of eight residues was synthesized from three template DNAs. In addition, a linear peptide composed of 13 residues was also synthesized by a similar method except that N-acetyl-L-alanine was used instead of N-chloroacetyl-L-phenylalanine.

As a result of analysis of the translation product by MALDI-TOF-MS, it was confirmed that an intended peptide was synthesized (FIG. 8). The results have suggested that a peptide library can be constructed in a system in which the number of the aminoacyl tRNA synthase, wild-type tRNA, or free amino acid is limited or a system free of them.

[Method (Supplement)]

1. Synthesis of Cyclic N-Alkyl Amino Acid Serving as a Substrate of Flexizyme

Any of the cyclic N-alkyl amino acids and cyclic N-alkyl amino acids protected with BoC group were purchased from Watanabe Chemical, Sigma & Aldrich, TCI, or Bachem. The cyclic N-alkyl amino acid 12, 15, or 17 was converted into a cyanomethyl ester (CME) and the other amino acids were converted into 3,5-dinitrobenzyl ester (DBE) (Reference Document 26).

2. Aminoacylation of Microhelix RNA with N-Alkyl Amino Acid Using Flexizyme

A microhelix RNA and Flexizyme were prepared by in vitro transcription of an appropriate template (Reference Document 26). An aminoacylation efficiency was measured using the microhelix RNA.

The reaction was performed on ice using 25 μM of dFx (for DBE substrate) or eFx (for CME substrate), 25 μM of microhelix RNA, and 5 mM of a cyclic N-alkyl amino acid substrate in 0.1 M of Hepes-K buffer (pH 7.5, 20 mM of $MgCl_2$ and 20% DMSO), while controlling the total amount to 5 μL.

The reaction was performed in the following order. First, 50 μM of microhelix RNA (in 0.2 M Hepes-K buffer pH 7.5 (2.5 μL)) was heated at 95° C. for one minute, followed by cooling at room temperature for five minutes or more. For cyclic N-alkyl amino acid 10, Bicine (pH 9) was used instead of HEPES-KOH (pH 7.5). Then, $MgCl_2$ (100 mM, 1 μL) and dFx or eFx (250 μM, 0.5 μL) were added to the reaction mixture. The reaction was started by adding a cyclic N-alkyl amino acid (25 mM, 1 μL in DMSO) and the reaction mixture was incubated on ice for 1 hour, 3 hours, 6 hours, or 18 hours. For cyclic N-alkyl amino acid 17, 54 of 200 mM substrate was used instead of 25 mM substrate.

The reaction was terminated by adding 154 of a loading buffer (150 mM sodium acetate, pH 5, 10 mM EDTA, and 83% formamide).

The sample thus obtained was analyzed using 20% denaturing acid PAGE (50 mM sodium acetate pH 5, 6 M of urea). RNA was stained with ethidium bromide and analyzed using Pharos FX (BIO-RAD).

3. Preparation of tRNA$^{Asn-E2}$ Aminoacylated with Cyclic N-Alkyl Amino Acid tRNA$^{Asn-E2}$ was prepared by in vitro transcription of an appropriate template (Reference Document 30). The aminoacylation of tRNA$^{Asn-E2}$ was performed under the following conditions.

The reaction was performed on ice by using 25 µM of dFx (for DBE substrate) or eFx (for CME substrate), 25 µM of tRNA$^{Asn-E2}$, 20 mM of MgCl$_2$, and 5 mM of cyclic N-alkyl amino acid substrate in 0.1 M of Hepes-K buffer (pH 7.5, 20 mM of MgCl$_2$ and 20% DMSO), while controlling the total amount to 50 µL.

The reaction was performed in the following order. First, 50 µM of tRNA$^{Asn-E2}$ (in 0.2 M Hepes-K buffer, pH 7.5 (25 µL)) was heated at 95° C. for one minute, followed by cooling at room temperature for five minutes or more. For cyclic N-alkyl amino acid 10, Bicine (pH 9) was added instead of HEPES-KOH (pH 7.5). Then, MgCl$_2$ (100 mM, 10 µL) and dFx or eFx (250 µM, 5 µL) were added to the reaction mixture. The reaction was started by adding a cyclic N-alkyl amino acid (25 mM, 10 µL in DMSO) and the reaction mixture was incubated on ice. For cyclic N-alkyl amino acid 17, 54 of 200 mM substrate was used instead of 25 mM substrate.

The reaction was terminated by adding 1504 of 0.6M sodium acetate, pH 5.

The resulting RNA precipitated in ethanol was collected and rinsed twice with 70% ethanol containing 0.1 M of sodium acetate and once with 70% ethanol.

4. Preparation of Template DNA Encoding Peptide

A template DNA encoding Peptide 1 of FIG. 2A was prepared by the conventional method (Reference Document 13). Primers used for the other template DNAs are shown in Table 3. Primers used for preparation of a template DNA library are shown in Table 4. Appropriate forward primer and reverse primer were annealed and the resulting product was elongated with Taq DNA polymerase. The dsDNA thus obtained was amplified with Taq DNA polymerase by using appropriate forward primer and reverse primer. The template DNA thus prepared was purified by phenol/chloroform extraction and ethanol precipitation.

5. Preparation of Re-Constitution Type Cell-Free Translation System

Re-constitution type translation system was prepared by the conventional method (Reference Documents 28, 25, 44, 15).

6. Preparation of tRNA by Aminoacylation with aaRS in Translation System tRNA$^{fMet}$ (CAU), tRNA$^{Tyr}$ (CUA), tRNA$^{Arg}$ (CCG), and tRNA$^{Ser}$ (CAU) were prepared by in vitro transcription using an appropriate template DNA in accordance with a conventional method (Reference Document 45). tRNA$^{Trp}$ (CCA) was prepared by providing a precursor tRNA by in vitro transcription using an appropriate template DNA and then performing RNase P digestion.

7. Ribosome Synthesis of Peptide Containing Two Successive Cyclic N-Alkyl Amino Acids A translation reaction liquid containing 0.04 µM of template DNA, 0.5 mM of each of Met, Tyr, and Arg, 0.03 µM of MetRS, 0.02 µM of TyrRS, 0.03 µM of ArgRS, and 100 µM of cyclic N-alkylaminoacyl-tRNA$^{Asn-E2}$ (GGA) was incubated at 37° C. for 60 minutes. MALDI-TOF MS analysis was performed in linear positive mode of autoflex II (BRUKER DALTONICS) by desalting the translation product with C-TIP (Nikkyo Technos) and eluted with a CHCA saturated solution of 80% acetonitrile and 0.5% acetic acid.

8. Streptavidin Pull-Down Assay of a Biotinylated Random Peptide/mRNA/cDNA Complex for Spacer Optimization Biotinylated-tRNA$^{Asn-E2}$ and biotinylated-Phe-tRNA$^{fMet}$ (CAU) were prepared using Flexizyme (Reference Document 26). TRAP system was prepared by the conventional method. For optimization of a spacer sequence, a random NNT3 DNA library was transcribed and translated at 37° C. for 25 minutes in a Cys-depleted TRAP system containing a crude PCR mixture containing 1 µM of T7 RNA polymerase, 2.5 µM of puromycin-DNA linker, 40 µM of biotinylated-tRNA$^{Asn-E2}$ (GCA), and 10% v/v cDNA library to obtain a biotinylated peptide library. For the optimization of the length of a spacer, a Trp depleted TRAP system containing 20 µM of biotinylated Phe-tRNA$^{fMet}$ (CAU) was used instead.

After dissociation of ribosome by EDTA, reverse transcription of mRNA was performed using the primer shown in Table 5 and RNase H inactivated reverse transcriptase. The reverse transcription was terminated with EDTA. After neutralization of the solution with HEPES, the cDNA/mRNA complex on which biotinylated peptide was displayed was selectively collected using beads coated with streptavidin and quantitatively determined by real time PCR.

TABLE 3

| Names | Sequences | SEQ ID NO: |
|---|---|---|
| T7pEpsSD6M.F46 | TAATA CGACT CACTA TAGGG TTAAC TTTAA CAAGG AGAAA AACAT G | 25 |
| eSD6MY3SFlag.R40 | TC GTC CTT GTA GTC GGA GTA GTA GTA CAT GTTTT TCTCC T | 26 |
| T7ex5.F22 | GGCGT AATAC GACTC ACTAT AG | 27 |
| Flaguaa.R33 | CGAAGC TTA CTT GTC GTC GTC GTC CTT GTA GTC | 28 |
| T7pEpsSD6MY3.F37 | GGT TAACT TTAAC AAGGA GAAAA AC ATG TAC TAC TAC | 29 |
| eSD6MY3S2RY3.R40 | TATTAGTAGTAGTACCT AGAAGA GTAGTAGTACATGTTTT | 30 |
| T7pEpsSD6.F40 | GGCGT AATAC GACTC ACTAT AGGGT TAACT TTAAC AAGGA | 31 |
| RY3uaa2.R18 | TTATTAGTAGTAGTACCT | 32 |
| eSD6Mamb3.F37 | GGT TAACT TTAAC AAGGA GAAAA AC ATG TAG TAG TAG | 33 |

TABLE 3 -continued

| Names | Sequences | SEQ ID NO: |
|---|---|---|
| Mamb3LSRamb3uaa2.R40 | ATTA CTACTACTACCG AGAAAG CTACTACTACATGTTTTT | 34 |
| Mamb3FSRamb3uaa2.R40 | ATTA CTACTACTACCG AGAAAA CTACTACTACATGTTTTT | 35 |
| Mamb3FPRamb3uaa2.R40 | ATTA CTACTACTACCG AGGAAA CTACTACTACATGTTTTT | 36 |
| Mamb3LPRamb3uaa2.R40 | ATTA CTACTACTACCG AGGAAG CTACTACTACATGTTTTT | 37 |
| Mamb3LFRamb3uaa2.R40 | ATTA CTACTACTACCG AAAAAG CTACTACTACATGTTTTT | 38 |
| tRamb3uaa2.R19 | TTATTA CTACTACTACCGA | 39 |
| Mamb3LFPRamb3uaa2.R40 | TTA CTACTACTACCG AGGAAAAAG CTACTACTACATGTTT | 40 |
| Mamb3FSPRamb3uaa2.R40 | TTA CTACTACTACCG AGGAGAAAA CTACTACTACATGTTT | 41 |
| Mamb3LSPRamb3uaa2.R40 | TTA CTACTACTACCG AGGAGAAAG CTACTACTACATGTTT | 42 |
| Mamb3LFSRamb3uaa2.R40 | TTA CTACTACTACCG AGAAAAAG CTACTACTACATGTTT | 43 |
| Mamb3LFSPRamb3uaa2.R40 | TA CTACTACTACCG AGGAGAAAAAG CTACTACTACATGT | 44 |
| Mamb3YCRHRamb3uaa2.R40 | TA CTACTACTACCG ATGACGACAATA CTACTACTACATGT | 45 |
| Mamb3VTIARamb3uaa2.R40 | TA CTACTACTACCG AGCAATAGTAAC CTACTACTACATGT | 46 |
| Mamb3NSGDRamb3uaa2.R40 | TA CTACTACTACCG ATCACCACTATT CTACTACTACATGT | 47 |

TABLE 4

| Names | Sequences | SEQ ID NO: |
|---|---|---|
| T7SD8M2.F44 | ATACTAATACGACTCACTATAGGATTAAGGAGGTGATATTT ATG | 48 |
| SD8Mnnu2nncCR4.R40 | CCGCCGCCGCCG GCAGNNANNANNCATAAATATCACCTCC | 49 |
| SD8Mnnu2nncGQ4.R40 | CTGCTGCTGCTG GCAGNNANNANNCATAAATATCACCTCC | 50 |
| SD8Mnnu2nncCE4.R40 | CTCCTCCTCCTC GCAGNNANNANNCATAAATATCACCTCC | 51 |
| SD8Mnnu2nncCK4.R40 | CTTCTTCTTCTT GCAGNNANNANNCATAAATATCACCTCC | 52 |
| SD8Mnnu2nncCM4.R40 | CATCATCATCAT GCAGNNANNANNCATAAATATCACCTCC | 53 |
| SD8Mnnu2nncCW4.R40 | CCACCACCACCA GCAGNNANNANNCATAAATATCACCTCC | 54 |
| cCR4ua.R39 | CCCGCCTCCCGCCCCCGTCC TA CCGCCGCCGCCG GCAG | 55 |
| cCQ4ua.R39 | CCCGCCTCCCGCCCCCGTCC TA CTGCTGCTGCTG GCAG | 56 |
| cCE4ua.R39 | CCCGCCTCCCGCCCCCGTCC TA CTCCTCCTCCTC GCAG | 57 |
| cCK4ua.R39 | CCCGCCTCCCGCCCCCGTCC TA CTTCTTCTTCTT GCAG | 58 |
| cCM4ua.R39 | CCCGCCTCCCGCCCCCGTCC TA CATCATCATCAT GCAG | 59 |
| cCW4ua.R39 | CCCGCCTCCCGCCCCCGTCC TA CCACCACCACCA GCAG | 60 |
| SD8Mnnu2nncWM4.R40 | CATCATCATCAT CCAGNNANNANNCATAAATATCACCTCC | 61 |
| SD8Mnnu2nncWM3amb.R40 | CTACATCATCAT CCAGNNANNANNCATAAATATCACCTCC | 62 |
| SD8Mnnu2nncWM2amb2.R40 | CTACTACATCAT CCAGNNANNANNCATAAATATCACCTCC | 63 |
| SD8Mnnu2nncWMamb3.R40 | CTACTACTACAT CCAGNNANNANNCATAAATATCACCTCC | 64 |
| SD8Mnnu2nncWamb4.R40 | CTACTACTACTA CCAGNNANNANNCATAAATATCACCTCC | 65 |
| cWM4ua.R39 | CCCGCCTCCCGCCCCCGTCC TA CATCATCATCAT GCAG | 66 |
| cWM3ambua.R39 | CCCGCCTCCCGCCCCCGTCC TA CTACATCATCAT CCAG | 67 |

TABLE 4-continued

| Names | Sequences | SEQ ID NO: |
|---|---|---|
| cWM2amb2ua.R39 | CCCGCCTCCCGCCCCCGTCC TA CTACTACATCAT CCAG | 68 |
| cwMamb3ua.R39 | CCCGCCTCCCGCCCCCGTCC TA CTACTACTACAT CCAG | 69 |
| cWamb4ua.R39 | CCCGCCTCCCGCCCCCGTCC TA CTACTACTACTA CCAG | 70 |
| SD8nnu8WM4ua.R59 | TACATCATCATCATCCA GNNANNANNANNANNANNANNANN CATAAATATCACCTCCTT | 71 |

TABLE 5

| Names | Sequences | SEQ ID NO: |
|---|---|---|
| cCR4ua.R19 | TA CCGCCGCCGCCG GCAG | 72 |
| cCQ4ua.R19 | TA CTGCTGCTGCTG GCAG | 73 |
| cCE4ua.R19 | TA CTCCTCCTCCTC GCAG | 74 |
| cCK4ua.R19 | TA CTTCTTCTTCTT GCAG | 75 |
| cCM4ua.R19 | TA CATCATCATCAT GCAG | 76 |
| cCW4ua.R19 | TA CCACCACCACCA GCAG | 77 |
| cCR4ua.R19 | TA CCGCCGCCGCCG GCAG | 78 |
| cWM4ua.R18 | TA CATCATCATCAT CCAG | 79 |
| cWM3ambua.R18 | TA CTACATCATCAT CCAG | 80 |
| cWM2amb2ua.R18 | TA CTACTACATCAT CCAG | 81 |
| cWMamb3ua.R18 | TA CTACTACTACAT CCAG | 82 |
| cWamb4ua.R18 | TA CTACTACTACTA CCAG | 83 |

REFERENCE DOCUMENTS

1. Mattheakis, L. C., Bhatt, R. R. & Dower, W. J. An in vitro polysome display system for identifying ligands from very large peptide libraries. Proc. Natl. Acad. Sci. USA 91, 9022-9026 (1994).
2. Hanes, J. & Pluckthun, A. In vitro selection and evolution of functional proteins by using ribosome display. Proc. Natl. Acad. Sci. USA 94, 4937-4942 (1997).
3. Nemoto, N., MiyamotoSato, E., Husimi, Y. & Yanagawa, H. In vitro virus: Bonding of mRNA bearing puromycin at the 3'-terminal end to the C-terminal end of its encoded protein on the ribosome in vitro. FEBS Lett. 414, 405-408 (1997).
4. Roberts, R. W. & Szostak, J. W. RNA-peptide fusions for the in vitro selection of peptides and proteins. Proc. Natl. Acad. Sci. USA 94, 12297-12302 (1997).
5. Kawakami, T. & Murakami, H. Genetically encoded libraries of nonstandard peptides. J. Nucleic Acids 2012, 713510 (2012).
6. Millward, S. W., Fiacco, S., Austin, R. J. & Roberts, R. W. Design of cyclic peptides that bind protein surfaces with antibody-like affinity. ACS Chem. Biol. 2, 625-634 (2007).
7. Hayashi, Y, Morimoto, J. & Suga, H. In Vitro Selection of Anti-Akt2 Thioether-Macrocyclic Peptides Leading to Isoform-Selective Inhibitors. ACS Chem. Biol. 7, 607-613 (2012).
8. Hofmann, F. T., Szostak, J. W. & Seebeck, F. P. In vitro selection of functional lantipeptides. J. Am. Chem. Soc. 134, 8038-8041 (2012).
9. Morimoto, J., Hayashi, Y. & Suga, H. Discovery of Macrocyclic Peptides Armed with a Mechanism-Based Warhead: Isoform-Selective Inhibition of Human Deacetylase SIRT2. Angew. Chem. Int. Ed. 51, 3423-3427 (2012).
10. Schlippe, Y. V., Hartman, M. C., Josephson, K. & Szostak, J. W. In vitro selection of highly modified cyclic peptides that act as tight binding inhibitors. J. Am. Chem. Soc. 134, 10469-10477 (2012).
11. Merryman, C. & Green, R. Transformation of aminoacyl tRNAs for the in vitro selection of "drug-like" molecules. Chem. Biol. 11, 575-582 (2004).
12. Kawakami, T., Murakami, H. & Suga, H. Messenger RNA-programmed incorporation of multiple N-methyl-amino acids into linear and cyclic peptides. Chem. Biol. 15, 32-42 (2008).
13. Kawakami, T., Murakami, H. & Suga, H. Ribosomal synthesis of polypeptoids and peptoid-peptide hybrids. J. Am. Chem. Soc. 130, 16861-16863 (2008).
14. Subtelny, A. O., Hartman, M. C. & Szostak, J. W. Ribosomal synthesis of N-methyl peptides. J. Am. Chem. Soc. 130, 6131-6136 (2008).
15. Kawakami, T. et al. Diverse backbone-cyclized peptides via codon reprogramming. Nat. Chem. Biol. 5, 888-890 (2009).
16. Subtelny, A. O., Hartman, M. C. & Szostak, J. W. Optimal codon choice can improve the efficiency and fidelity of N-methyl amino acid incorporation into peptides by in-vitro translation. Angew. Chem. Int. Ed. 50, 3164-3167 (2012).
17. Yamagishi, Y. et al. Natural product-like macrocyclic N-methyl-peptide inhibitors against a ubiquitin ligase uncovered from a ribosome-expressed de novo library. Chem. Biol. 18, 1562-1570 (2011).
18. Ellman, J. A., Mendel, D. & Schultz, P. G. Site-specific incorporation of novel backbone structures into proteins. Science 255, 197-200 (1992).
19. Chung, H. H., Benson, D. R., Cornish, V. W. & Schultz, P. G. Probing the role of loop 2 in Ras function with unnatural amino acids. Proc. Natl. Acad. Sci. USA 90, 10145-10149 (1993).
20. Chung, H. H., Benson, D. R. & Schultz, P. G. Probing the structure and mechanism of Ras protein with an expanded genetic code. Science 259, 806-809 (1993).
21. Deming, T. J. F., M. J.; Mason, T. L.; Tirrell, D. A. Structural Modification of a Periodic Polypeptide Through Biosynthetic Replacement of Proline with Azetidine-2-Carboxylic Acid. Macromolecules 29, 1442-1444 (1996).
22. Deming, T. J., Fournier, M. J., Mason, T. L. & Tirrell, D. A. Biosynthetic incorporation and chemical modification of alkene functionality in genetically engineered polymers. J. Macromol. Sci. A: Pure Appl. Chem. 34, 2143-2150 (1997).

23. Steiner, T. et al. Synthetic biology of proteins: tuning GFPs folding and stability with fluoroproline. PLoS One 3, e1680 (2008).
24. Forster, A. C. et al. Programming peptidomimetic syntheses by translating genetic codes designed de novo. Proc. Natl. Acad. Sci. USA 100, 6353-6357 (2003).
25. Josephson, K., Hartman, M. C. T. & Szostak, J. W. Ribosomal synthesis of unnatural peptides. J. Am. Chem. Soc. 127, 11727-11735 (2005).
26. Murakami, H., Ohta, A., Ashigai, H. & Suga, H. A highly flexible tRNA acylation method for non-natural polypeptide synthesis. Nat. Methods 3, 357-359 (2006).
27. Forster, A. C., Weissbach, H. & Blacklow, S. C. A simplified reconstitution of mRNA-directed peptide synthesis: activity of the epsilon enhancer and an unnatural amino acid. Anal. Biochem. 297, 60-70 (2001).
28. Shimizu, Y. et al. Cell-free translation reconstituted with purified components. Nat. Biotechnol. 19, 751-755 (2001).
29. Hartman, M. C., Josephson, K., Lin, C. W. & Szostak, J. W. An expanded set of amino acid analogs for the ribosomal translation of unnatural peptides. PLoS One 2, e972 (2007).
30. Ohta, A., Murakami, H., Higashimura, E. & Suga, H. Synthesis of polyester by means of genetic code reprogramming. Chem. Biol. 14, 1315-1322 (2007).
31. Forster, A. C. Low modularity of aminoacyl-tRNA substrates in polymerization by the ribosome. Nucleic Acids Res 37, 3747-3755 (2009).
32. Forster, A. C. Synthetic biology challenges long-held hypotheses in translation, codon bias and transcription. Biotechnol J 7, 835-845 (2012).
33. Zhang, B. et al. Specificity of translation for N-alkyl amino acids. J. Am. Chem. Soc. 129, 11316-11317 (2007).
34. Heckler, T. G. et al. T4 RNA ligase mediated preparation of novel "chemically misacylated" tRNAPheS. Biochemistry 23, 1468-1473 (1984).
35. Murakami, H., Hohsaka, T., Ashizuka, Y. & Sisido, M. Site-directed incorporation of p-nitrophenylalanine into streptavidin and site-to-site photoinduced electron transfer from a pyrenyl group to a nitrophenyl group on the protein framework. J. Am. Chem. Soc. 120, 7520-7529 (1998).
36. Murakami, H., Hohsaka, T., Ashizuka, Y, Hashimoto, K. & Sisido, M. Site-directed incorporation of fluorescent nonnatural amino acids into streptavidin for highly sensitive detection of biotin. Biomacromolecules 1, 118-125 (2000).
37. Murakami, H., Kourouklis, D. & Suga, H. Using a solid-phase ribozyme aminoacylation system to reprogram the genetic code. Chem. Biol. 10, 1077-1084 (2003).
38. Hartman, M. C., Josephson, K. & Szostak, J. W. Enzymatic aminoacylation of tRNA with unnatural amino acids. Proc. Natl. Acad. Sci. USA 103, 4356-4361 (2006).
39. Ohuchi, M., Murakami, H. & Suga, H. The flexizyme system: a highly flexible tRNA aminoacylation tool for the translation apparatus. Curr. Opin. Chem. Biol. 11, 537-542 (2007).
40. Xiao, H., Murakami, H., Suga, H. & Ferre-D'Amare, A. R. Structural basis of specific tRNA aminoacylation by a small in vitro selected ribozyme. Nature 454, 358-361 (2008).
41. Eggertsson, G. & Soll, D. Transfer ribonucleic acid-mediated suppression of termination codons in *Escherichia coli*. Microbiol. Rev. 52, 354-374 (1988).
42. Cochella, L. & Green, R. An active role for tRNA in decoding beyond codon:anticodon pairing. Science 308, 1178-1180 (2005).
43. Johansson, M., Lovmar, M. & Ehrenberg, M. Rate and accuracy of bacterial protein synthesis revisited. Curr. Opin. Microbiol. 11, 141-147 (2008).
44. Ledoux, S., Olejniczak, M. & Uhlenbeck, O. C. A sequence element that tunes *Escherichia coli* tRNA(Ala)(GGC) to ensure accurate decoding. Nat. Struct. Mol. Biol. 16, 359-364 (2009).
45. Murakami, H., Ohta, A. & Suga, H. Bases in the anticodon loop of tRNA(Ala)(GGC) prevent misreading. Nat. Struct. Mol. Biol. 16, 353-358 (2009).
46. Zaher, H. S. & Green, R. Fidelity at the molecular level: lessons from protein synthesis. Cell 136, 746-762 (2009).
47. O'Donoghue, P. et al. Near-cognate suppression of amber, opal and quadruplet codons competes with aminoacyl-tRNA(Pyl) for genetic code expansion. FEBS Lett. 586, 3931-3937 (2012).
48. Kawakami, T., Ishizawa, T., Fujino, T., Reid, P. C., Suga, H., Murakami, H. In vitro selection of multiple libraries created by genetic code reprogramming to discover macrocyclic peptides that antagonize VEGFR2 activity in living cells. ACS Chem. Biol., in press.
49. Ishizawa, T., Kawakami, T., Reid, P. C., Murakami, H. TRAP display: a high-speed selection method for the generation of functional polypeptides. J. Am. Chem. Soc. 2013, 135, (14), 5433-40.

The invention claimed is:

1. A method for producing a peptide library including $1 \times 10^6$ or more peptides containing amino acids encoded by $N_1N_2N_3$, comprising:

a step of preparing an mRNA library including mRNAs which encode peptides of the peptide library, respectively, and each contain a plurality of $N_1N_2N_3$s; and a step of translating each of the mRNAs of the mRNA library in a cell-free translation system added with a tRNA containing an anticodon to any of $N_1N_2N_3$ codons and charged with an amino acid corresponding to the codon, wherein $N_1$, $N_2$, and $N_3$ are each independently selected from adenine (A), guanine (G), cytosine (C), and uracil (U); and an arbitrary amino acid is reassigned to each $N_1N_2N_3$ and $N_1N_2U$ codons are reassigned to non-proteinogenic amino acids, and wherein the amino acids encoded by $N_1N_2N_3$ contain a non-proteinogenic amino acid selected from cyclic N-alkyl amino acids represented by chemical structures 2 to 22:

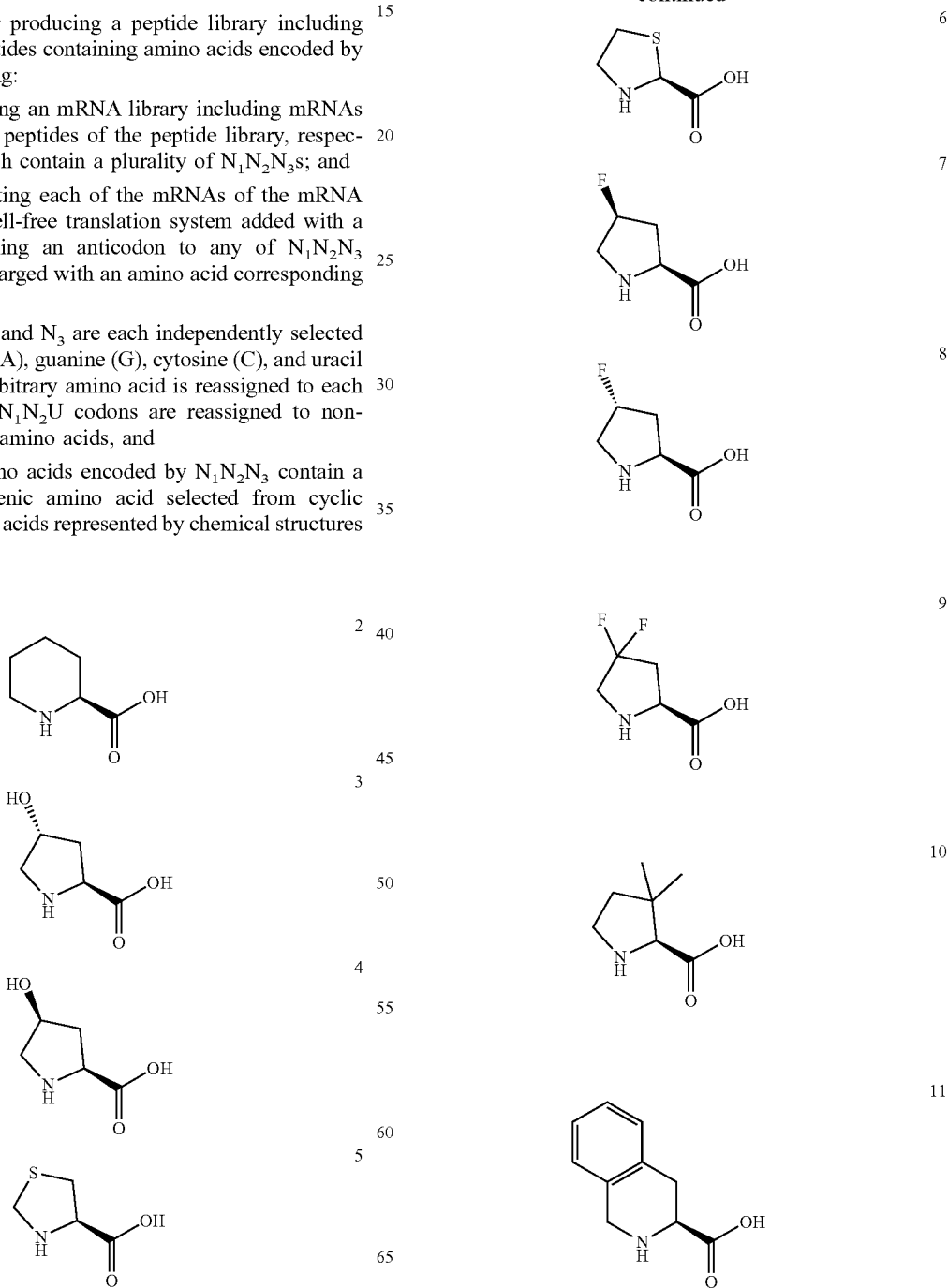

12

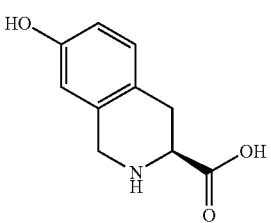

13

14

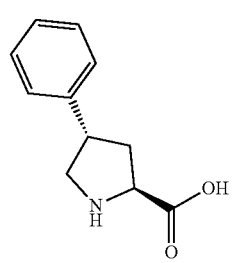

15

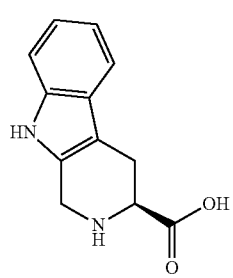

16

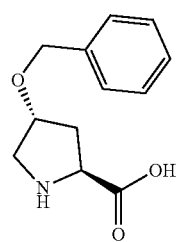

17

18

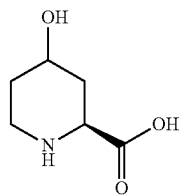

19

20

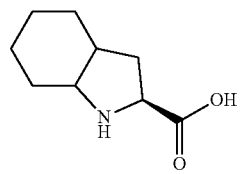

21

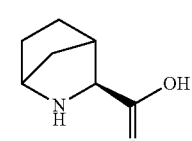

22

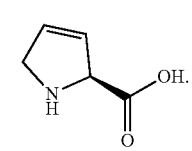

2. The method according to claim 1, wherein each of the mRNAs included in the mRNA library is represented by the following formula (I):

$$X_1—(N_1N_2N_3)n\text{-}X_2 \qquad (I)$$

wherein, $X_1$ and $X_2$ each represent an mRNA encoding a peptide composed of an arbitrary number of amino acids; and n stands for an arbitrary integer selected from 4 to 20.

3. The method according to claim 1,
wherein the peptide library is a peptide-mRNA complex library in which each peptide is complexed with an mRNA encoding the peptide,
wherein the mRNA library is a puromycin-bound mRNA library each mRNA has puromycin bound to a downstream region of ORF in the mRNA; and
the step of translating produces a peptide-mRNA complex library.

4. The method according to claim 3, wherein each of the mRNAs included in the puromycin-bound mRNA library is represented by the following formula (I):

$$X_1—(N_1N_2N_3)n\text{-}X_2 \qquad (I)$$

wherein, $X_1$ and $X_2$ each represent an mRNA encoding a peptide having an arbitrary number of amino acids and n stands for an arbitrary integer selected from 4 to 20.

5. The method according to claim 1, wherein the $N_3$ is either the following (i) or (ii) in one translation system:
  (i) cytosine (C) or uracil (U);
  (ii) adenine (A) or guanine (G).

6. The method according to claim 1, wherein 16 kinds of the $N_1N_2N_3$s are present in one translation system.

7. The method according to claim 1, wherein, of the tRNAs charged with an amino acid corresponding to the $N_1N_2N_3$ codon, elongator tRNAs have base sequences having 85% or more sequence homology with each other, respectively.

8. The method according to claim 1, wherein, of the tRNAs charged with an amino acid corresponding to the $N_1N_2N_3$ codon, elongator tRNAs have RNA sequences identical to each other except for an anticodon loop, respectively.

9. The method according to claim 1, further comprising, after the translation step, a peptide macrocyclization step.

10. A screening method for identifying a peptide to be bound to a target substance, comprising:
    a step of producing the peptide library according to claim 1 and bringing the peptide library into contact with the target substance, followed by incubation; and
    a step of selecting the peptide bound to the target substance.

11. A screening method for identifying a peptide to be bound to a target substance, comprising:
    a step of producing the peptide library according to claim 3 and subjecting the peptide-mRNA complex library to a reverse transcription reaction to obtain a peptide-DNA complex library;
    a step of bringing the peptide-DNA complex library into contact with the target substance, followed by incubation;
    a step of selecting a peptide-DNA complex group bound to the target substance;
    a step of amplifying DNA of the selected peptide-DNA complex group by PCR; and
    a step of transcribing the amplified DNA to produce an mRNA library, binding puromycin to a downstream region of ORF in the mRNA to produce a puromycin-bound mRNA library, and translating it to produce a peptide-mRNA complex library,
    wherein the steps from the reverse transcription reaction to the production of the peptide-mRNA complex library is repeated twice or more to select a peptide having high affinity for the target substance.

12. The screening method according to claim 11, wherein the $N_3$ is either the following (i) or (ii) in one translation system:
    (i) cytosine (C) or uracil (U);
    (ii) adenine (A) or guanine (G).

13. The screening method according to claim 11, wherein 16 kinds of the $N_1N_2N_3$s are present in one translation system.

14. The screening method according to claim 11, wherein, of the tRNAs charged with an amino acid corresponding to the $N_1N_2N_3$ codon, elongator tRNAs have base sequences having 85% or more sequence homology with each other, respectively.

15. The screening method according to claim 11, wherein, of the tRNAs charged with an amino acid corresponding to the $N_1N_2N_3$ codon, elongator tRNAs have RNA sequences identical to each other except for an anticodon loop, respectively.

16. The screening method according to claim 11, further comprising, after the translation step, a peptide macrocyclization step.

17. The screening method for identifying a peptide to be bound to a target substance according to claim 10, comprising:
    a step of bringing the peptide library into contact with the target substance, followed by incubation; and
    a step of selecting the peptide bound to the target substance, wherein the mRNA library is represented by the following formula (I):

$$X_1-(N_1N_2N_3)n-X_2 \qquad (I)$$

wherein $X_1$ and $X_2$ each represent an mRNA encoding a peptide having an arbitrary number of amino acids; and n stands for an arbitrary integer selected from 4 to 20.

18. The screening method for identifying a peptide to be bound to a target substance according to claim 17, comprising:
    a step of subjecting the peptide-mRNA complex library, wherein each peptide is complexed with an mRNA encoding the peptide, to a reverse transcription reaction to obtain a peptide-DNA complex library;
    a step of bringing the peptide-DNA complex library into contact with the target substance, followed by incubation;
    a step of selecting a peptide-DNA complex group bound to the target substance;
    a step of amplifying DNA of the selected peptide-DNA complex group by PCR; and
    a step of transcribing the amplified DNA to produce an mRNA library, binding puromycin to a downstream region of ORF in the mRNA to produce a puromycin-bound mRNA library, and translating it to produce a peptide-mRNA complex library,
    wherein the steps from the reverse transcription reaction to the production of the peptide-mRNA complex library is repeated twice or more to select a peptide having high affinity for the target substance.

* * * * *